US007297487B2

(12) United States Patent
Sakamoto

(10) Patent No.: US 7,297,487 B2
(45) Date of Patent: Nov. 20, 2007

(54) DESMIN GENE HAVING NOVEL POINT MUTATION CAUSATIVE OF DILATED CARDIOMYOPATHY

(75) Inventor: Aiji Sakamoto, Toyonaka (JP)

(73) Assignee: Japan Science and Technology Agency, Saitama (JP)

( * ) Notice: Subject to any disclaimer, the term of this patent is extended or adjusted under 35 U.S.C. 154(b) by 463 days.

(21) Appl. No.: 10/495,409

(22) PCT Filed: Oct. 11, 2002

(86) PCT No.: PCT/JP02/10569

§ 371 (c)(1),
(2), (4) Date: May 12, 2004

(87) PCT Pub. No.: WO03/042386

PCT Pub. Date: May 22, 2003

(65) Prior Publication Data

US 2005/0155092 A1    Jul. 14, 2005

(30) Foreign Application Priority Data

Nov. 12, 2001  (JP) ............................. 2001-345491
Feb. 12, 2002  (JP) ............................. 2002-034379

(51) Int. Cl.
*C12Q 1/68* (2006.01)
(52) U.S. Cl. ................... 435/6; 435/91.1; 435/91.2
(58) Field of Classification Search ................. None
See application file for complete search history.

(56) References Cited

OTHER PUBLICATIONS

Quax et al. Cell vol. 43:327-338. 1985.*
Park et al. Clinical Genetics vol. 57:423-1-429. 2000.*
Dalakas et al., *New England Journal of Medicine*, 342(11p):770-780 (2000).
Database Medline, National Library of Medicine, PMID: 11061256, Sugawara et al., *Neurology*, 55(7):986-990 (2000).
Database Medline, National Library of Medicine, PMID: 10905661, Park et al., *Clin. Genet.*, 57(6):423-439 (2000).
Birkenberger et al., *J. Cell. Biol.*, 111(5, Part 1):2063-2075 (1990).
Kawada et al., *Biochem. Biophys. Res. Commun.*, 284(2):431-435 (2001).
Sakamoto et al., *Japanese Journal of Pharmacology*, 88(Suppl. 1):66P-P-17 (2002).

P. Vicart et al. "Human desmin gene: cDNA sequence, regional localization and exclusion of the locus in a familial desmin-related myopathy" *Human Genetics*, vol. 98, No. 4, 1996, pp. 422-429, XP002325483.
Database EMBL Online! Mar. 9, 1987, "Hamster desmin gene encoding the intermediate filament (IF) protein desmin, exons 1, 2, 3, 4, 5 and 6" XP002325534.
B. Goudeau et al. "Structural and functional analysis of a new desmin variant causing desmin-related myopathy" *Human Mutation*, vol. 18, No. 5, 2001, pp. 388-396, XP002325484.
G. Sjöberg et al. "A missense mutation in the desmin rod domain is associated with autosomal dominant distal myopathy, and exerts a dominant negative effect on filament formation" *Human Molecular Genetics*, vol. 8, No. 12, Nov. 1999, pp. 2191-2198, XP002325485.
A. Muñoz-Mármol et al. "A dysfunctional desmin mutation in a patient with severe generalized myopathy" *Proceedings of the National Academy of Sciences of the United States of America*, vol. 95, No. 19, Sep. 15, 1998, pp. 11312-11317, XP002325486.
Database EMBL[online ]Mar. 13, 1998 "Gallus gallus mRNA for desmin, partial CDs", retrieved from EBI Database accession No. AB011672.
D. Li et al., "Desmin Mutation Responsible for Idiopathic Dilated Cardiomyopathy", *Circulation*, pp. 461-464 (1999).

* cited by examiner

*Primary Examiner*—Gary Benzion
*Assistant Examiner*—Heather Calamita
(74) *Attorney, Agent, or Firm*—David G. Conlin; Christine C. O'Day; Edwards Angell Palmer & Dodge LLP

(57) ABSTRACT

The present invention is intended to elucidate the cause of severe cardiomyopathy in subline (T) not manifesting the macroscopic cardiac hypertrophy, which has been separated from a hamster (B) with hypertrophic cardiomyopathy and clarify the pathogenic cause of dilated cardiomyopathy, thereby establishing a method of detecting and identifying dilated cardiomyopathy and a method of preventing and treating the same. The present invention relates to a desmin gene having a point mutation at the site corresponding to the 571-position of the base sequence in the cDNA translation region of Syrian hamster; a polypeptide thereof; and an oligonucleotide consisting of 5 to 250 bases including the point mutation site or an oligonucleotide having a sequence complementary thereto. Moreover, the present invention relates to a method of detecting and identifying the point mutation at the site corresponding to the 571-position of the base sequence in the cDNA translation region of Syrian hamster to judge whether or not it is a gene causative of hereditary cardiomyopathy.

6 Claims, 14 Drawing Sheets

```
Golden  TACATCGAGA AAGTGCGCTT CTTGGAGCAG CAGAACGCCG CGCTCGCCGC TGAGGTCAAC  420
TO-2    .......... .......... .......... .......... .......... ..........
              DesF →

Golden  CGGCTCAAGG GCCGCGAGCC GACCCGGGTC GCCGAGCTCT ATGAGGAGGA GATGCGCGAG  480
TO-2    .......... .......... .......... .......... .......... ..........

Golden  CTGCGGGCGCC AGGTGGAGGT GCTCACCAAC CAGCGTGCCC GTGTCGACGT GGAGCGCGAC  540
TO-2    .......... .......... .......... .......... .......... ..........

Golden  AACTTGATCG ACGACCTCCA GAGGCTCAAG GCCAAgtgag ggcacggcgc ctcctagatc  575
TO-2    .......... .......... .......... .......... A......... ..........
                                              ← DesGR
                                                    ← DesTR
```

B

Golden    BIO14.6    TO-2

G  A

DESMIN GENE HAVING NOVEL POINT MUTATION CAUSATIVE OF DILATED CARDIOMYOPATHY

TECHNICAL FIELD

The present invention has clarified a gene causative of hereditary cardiomyopathy. The present invention relates to a desmin gene having a point mutation at the site corresponding to the 571-position of the base sequence in the desmin cDNA translated region of Syrian hamster; to a mutant protein; to an oligonucleotide containing the point mutation site; and to a method of detecting and identifying the hereditary cardiomyopathy using the same. The invention also relates to an animal model for disease containing only the mutant desmin gene.

BACKGROUND ART

Heart is an important organ to deliver blood to the whole body. The cardiac muscle plays a key role in order for a heart to work as a pump. The cardiac muscle, though involuntary, is striated like skeletal muscle. Striated muscle is the muscle tissue named so because of its striated appearance of the sarcomere due to the alignment of dark bands (myosin filament region) and light bands (Z-line region at each end of sarcomere) caused by the arrangement of actin filaments and myosin filaments in the myofibrils. Muscle cell is an elongate fibrous cell, containing numerous myofibrils and mitochondria in its cytoplasm (sarcoplasm), and is enclosed within the cell membrane called sarcolemma (sarcoplasmic membrane).

A myofibril in the sarcoplasm consists of sarcomeres which are the assemblies of actin filaments and myosin filaments. And the thinner transverse line of Z-line exists in between sarcomeres. T-tubule is located close to the Z-line, which instantly propagates the electrical excitation transmitted over the surface of sarcolemma into a myofibril, the interior of muscle cell. The electrical excitation propagated into muscle cell is then led to sarcomere via T-tubule, thereby initiated a contraction.

Cardiac muscle made up with the reticulum of muscle fibers (cardiac muscle cells) that spirally surrounds the heart, delivers blood to the whole body by repeated autonomous contractions. When heart is overloaded for a long period, cardiac muscle tissue enlarges itself not by cell division but increasing length and width of each cardiac muscle cell. That is called myocardial hypertrophy. When weight of the heart exceeds 500 g, insufficient supply of blood to cardiac muscle cells occurs because the coronary artery or the like which supply oxygen and nutrition to cardiac muscle cells are undevelopable in compensation for the hypertrophy thereof.

Cardiomyopathy is a disease resulting from abnormality of myocardium. Heart being a life-sustaining organ, and yet non-regenerative, cardiomyopathy is a severe progressive degenerative disease thereof. Cardiomyopathy is classified into a primary cardiomyopathy such as dilated (congestive) and hypertrophic cardiomyopathy; and a secondary cardiomyopathy such as infectious cardiomyopathy. The primary cardiomyopathy is categorized into hypertrophic cardiomyopathy caused by hypertrophy of cardiac muscle and dilated cardiomyopathy caused by other factors.

Cardiomyopathic hamster, a representative animal model for hereditary cardiomyopathy, was found in 1962 and has been studied in various fields such as pathology, pharmacology and physiology. A serious cardiomyopathic subline (TO-2; hereinafter, abbreviated to "T") not manifesting the macroscopic cardiac hypertrophy has been established from a prototype of the hypertrophic cardiomyopathic hamster BIO 14.6 (hereinafter, abbreviated to "B").

FIG. 1 is a photograph as a drawing showing the characteristics of those cardiomyopathic hamsters. G in the left hand side of FIG. 1 is a normal Golden hamster, B in the middle is a hypertrophic cardiomyopathic BIO 14.6 hamster and T in the right hand side is a dilated cardiomyopathic TO-2 hamster. FIG. 1(A) in the top row shows the optical microscopic feature of left ventricle for each hamster stained with hematoxylin and eosin. Necrosis, fibrosis and calcification have been observed in both B and T. The bar in (A) represents 200 μm. FIG. 1(B) shows the horizontal cross sectional feature of left ventricle of each hamster. Compensated hypertrophy in residual myocardium is significant in B, while ventricle wall is remarkably thin in T. The bar in (B) represents 2 mm. FIG. 1(C) in the bottom row shows precordial lead V1 of electrocardiogram for each hamster. Potentials of QRS complexes in Golden (G), BIO 14.6 (B) and TO-2 (T) are 0.55±0.06, 0.98±0.06 and 0.22±0.06 V, respectively. In (C), the vertical bar represents 0.5 V; the horizontal bar represents one second.

The present inventors have clarified that genetic abnormality common in the cardiomyopathic hamster is due to the deletion of δ-sarcoglycan gene which is one of dystrophin-associated proteins (Sakamoto, A., et al., *Proc. Natl. Acad. Sci. U. S. A.*, 1997, 94 (13873-13878); Sakamoto, A., et al., *FEBS Lett.*, 1999, 447, 124-128).

However, it is not appropriate to discuss the cause of the cardiomyopathy of hamsters only in view of δ-sarcoglycan deficiency since the macroscopic hypertrophy of cardiac muscle has not been observed in hamster T. Further investigation with reference to the cause of cardiomyopathy in hamster (T) has been required.

DISCLOSURE OF THE INVENTION

An object of the invention is to elucidate the cause of severe cardiomyopathy in subline (T) not manifesting the macroscopic hypertrophy of cardiac muscle, which has been separated from a hamster BIO 14.6 (B) with hypertrophic cardiomyopathy and clarify the pathogenic cause of dilated cardiomyopathy, thereby establishing a method of preventing and treating the same.

Further to the above, the invention is to provide a novel animal model for disease comprising only subline T which has gene causative of cardiomyopathy and to provide a method of developing or evaluating a novel therapy (such as pharmaceuticals, genetic therapy and regenerative medicine) for treating hereditary cardiomyopathy using such an animal.

Still another object of the present invention is to provide a means for elucidating a linkage mechanism between myofibril and sarcoplasmic membrane (including T-tubules) in cardiac muscle using TO-2 hamster or the subline thereof.

BRIEF DESCRIPTION OF THE DRAWINGS

FIG. 9 shows a base sequence of desmin cDNA (SEQ ID NO: 1) of normal Syrian hamster and point mutation in TO-22 . The amino acid translation (SEQ ID NO: 2) is shown by one-letter code above the corresponding codon. The allotted base numbers cover only the translated region of the sequence. Desmin cDNA which covers the whole translated region can be obtained by ligating the RT-PCR products prepared with primer sets of Des5F/Des5R and Des3F/Des3R at the recognition site of restriction endonuclease (Sal I) marked by box (refer to FIG. 12). The primers to amplify four domains of desmin (refer to FIG. 14) are specified as well. A point mutation (G571A) exists in desmin of TO-2 (refer to FIG. 13), thereby the 191st amino acid normal A (alanine) is altered to T (threonine).

FIG. 13 is a photograph as a drawing which shows a base mutation of genome in a dilated cardiomyopathic hamster TO-2 and detection thereof by a PCR. FIG. 13(A) shows the base sequences of genome adjacent to the point mutation (G571A) site of desmin gene in normal Golden hamster (SEQ ID NO: 3) and dilated cardiomyopathic hamster TO-2 (SEQ ID NO: 4), wherein the bases identical in both sequences are indicated by dots (.). Base sequences in the first exon and in the first intron are indicated by uppercase and lowercase respectively. Base numbers correspond to those of the cDNA sequence in FIG. 9. Examples of the primers used for genetic diagnosis are shown by arrows. FIG. 13(B) is a photograph as a drawing which shows the result of genomic PCR using the primer set (DesF/DesGR) or (DesF/DesTR) shown by arrows. Alleles in those sites are (G/G), (G/G) and (A/A), respectively.

FIG. 14(A) shows four domains of desmin by a schematic diagram. Amino acid mutaintion in TO-2 is marked with a circle (○). FIG. 14(B) is a photograph as a drawing which shows full length of desmin and expression of recombinant protein in each domain. cDNA of each domain was amplified using the primer sets as shown in FIG. 9, inserted into an expression vector pET33b and expressed in *Escherichia coli* BL21 (DE3). The whole lysate of each *Escherichia coli* was subjected to SDS-PAGE and stained with CBB. The band corresponding to the aimed protein was marked with *. Lane 1 shows the full length of desmin, lane 2 shows a head domain, lane 3 shows coil-2 domain, lane 4 shows a tail domain, lane 5 shows coil-1 domain (191A) of normal hamster and lane 6 shows the mutated coil-1 domain (191T).

BEST MODE FOR CARRYING OUT THE INVENTION

Figure 1:
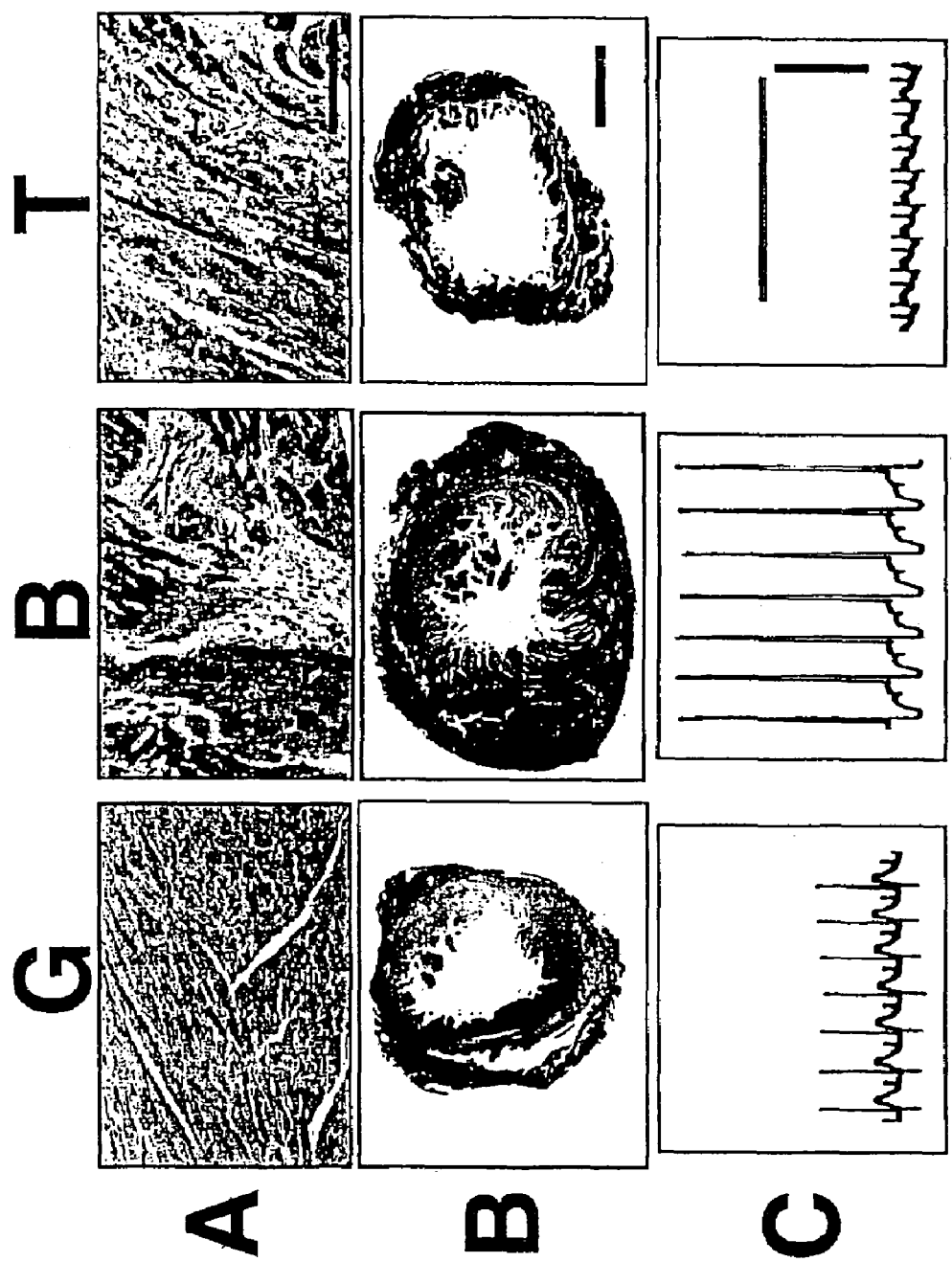
FIG. 1 is a photograph as a drawing which shows the characteristics of normal hamster and cardiomyopathic hamster. G in FIG. 1 shows a normal Golden hamster, B shows a hypertrophic cardiomyopathic BIO 14.6 hamster and T shows a dilated cardiomyopathic TO-2 hamster. (A) in FIG. 1 shows an optical microscopic feature of left ventricle of each hamster stained with hematoxylin and eosin, (B) shows a horizontal cross sectional feature thereof and (C) shows a periodical lead V1 of electrocardiogram for those hamsters.

The invention relates to a desmin gene having a point mutation at the site corresponding to the 571-position of the base sequence in the desmin cDNA translated region of Syrian hamster, particularly to the desmin gene having a point mutation from G to A.

The invention relates to oligonucleotides comprising 5 to 250 bases including the site corresponding to the 571-position of the base sequence in the desmin cDNA translated region of Syrian hamster or to oligonucleotides having sequence complementary thereto.

The invention further relates to a method of detecting and identifying a point mutation in the desmin gene at the site corresponding to the 571-position of a base sequence in the cDNA translated region of Syrian hamster in order to judge whether or not it is a gene causative of hereditary cardiomyopathy. To be more spesific, it relates to a method of detecting and identifying a point mutation using a PCR or a method using the above-described oligonucleotides.

The invention further relates to a primer for the above PCR or a primer for the amplification of each domain of desmin.

The invention relates to a kit for detecting and identifying a point mutation in the desmin gene at the site corresponding to the 571-position of a base sequence in the cDNA translated region of Syrian hamster using the above-mentioned primers or oligonucleotides.

The invention also relates to desmin encoded by a desmin gene having a point mutation at the site corresponding to the 571-position of the base sequence in the desmin cDNA translated region of Syrian hamster; to a polypeptide comprising desmin's head domain, coil-1 domain, coil-2 domain or tail domain; to a polypeptide where alanine, the 191st amino acid in coil-1 domain, is mutated to threonine; and to an antibody against such polypeptides.

The invention further relates to an animal model for disease wherein the genetic abnormality is caused only by the desmin gene having a point mutation at the site corresponding to the 571-position of the base sequence in the desmin cDNA translated region of Syrian hamster; to be more specific, to an animal model for hereditary cardiomyopathy obtained by subjecting TO-2 hamster to crossbreeding with other hamsters, normal hamsters for example; and to a method of preventing and treating the hereditary cardiomyopathy using such an animal model for disease, as well as to a method for screening the preventive and therapeutic agent.

Severe subline (TO-2; hereinafter, abbreviated as "T") not manifesting macroscopic cardiac hypertrophy has been separated from the hypertrophic cardiomyopathic hamster BIO 14.6 (hereinafter, abbreviated as "B") which is a prototype of cardiomyopathic hamster and is a representative animal model for hereditary cardiomyopathy.

The present inventors have revealed that genetic abnormality common in those cardiomyopathic hamsters is due to the deficiency of δ-sarcoglycan gene which is one of dystrophin-associated proteins (Sakamoto, A., et al., *Proc. Natl. Acad. Sci. U. S. A.*, 1997, 94 (13873-13878); Sakamoto, A., et al., *FEBS Lett*, 1999, 447, 124-128). However, hypertrophy of cardiac muscle being not observed in hamster T, it is not appropriate to discuss the cause of those hamsters' cardiomyopathy only by limiting to the deficiency of δ-sarcoglycan gene. Further investigation has been required for clarifying the cause of cardiomyopathy in hamster T.

Figure 2:
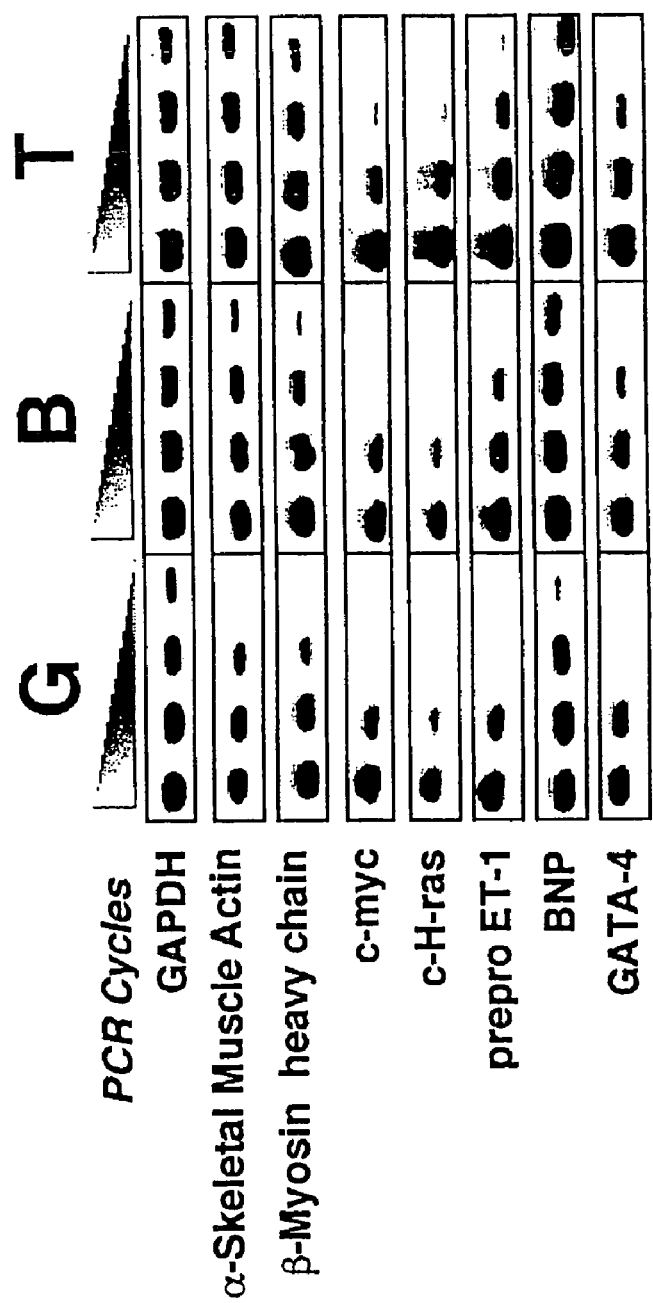
FIG. 2 is a photograph as a drawing which shows the result of quantitative determination of cardiac hypertrophy-related gene by an RT-PCR of normal hamster and cardiomyopathic hamster. G in FIG. 2 shows a normal Golden hamster, B shows a hypertrophic cardiomyopathic BIO 14.6 hamster and T shows a dilated cardiomyopathic TO-2 hamster. PCR cycles are 40, 35, 30 and 25, respectively from the left side. GAPDH (glyceraldehye 3-phosphate dehydrogenase) was used as an internal control.

Due to the pressure load or low-oxygen load, cardiac muscle cell is characterized to be enlarged by increase of its volume not by cell division (compensated cardiac hypertrophy). Firstly therefore, expressed amount of gene relating thereto was analyzed by RT-PCR. The result is shown in FIG. 2 by a photograph as a drawing. G in the left hand side of FIG. 2 is a normal Golden hamster, B in the middle is a hypertrophic cardiomyopathic BIO 14.6 hamster and T in the right hand side is a dilated cardiomyopathic TO-2 hamster. Each row from the top in FIG. 2 represents GAPDH (glyceraldyde 3-phosphate dehydrogenase) which is the internal control; α-skeletal muscle actin; β-myosin heavy chain; c-myc; c-H-ras; prepro-endothelin-1; brain natriuretic peptide (BNP) and GATA-4, respectively. PCR cycles are 40, 35, 30 and 25 from the left. The larger gene expression amount becomes, the further to the right the band is detected. The identical amount of amplification of GAPDH (glyceraldyde 3-phosphate dehydrogenase: an internal control) being detected in respective samples, cDNA from Golden (G), BIO 14.6 (B) and TO-2 (T) used for analysis has been confirmed to be the same amount.

Unexpectedly as a result, the expression of genes relating to the cardiac hypertrophy such as prepro-endothelin-1, c-myc and β-myosin heavy chain was detected more in T than in B.

Figure 3:
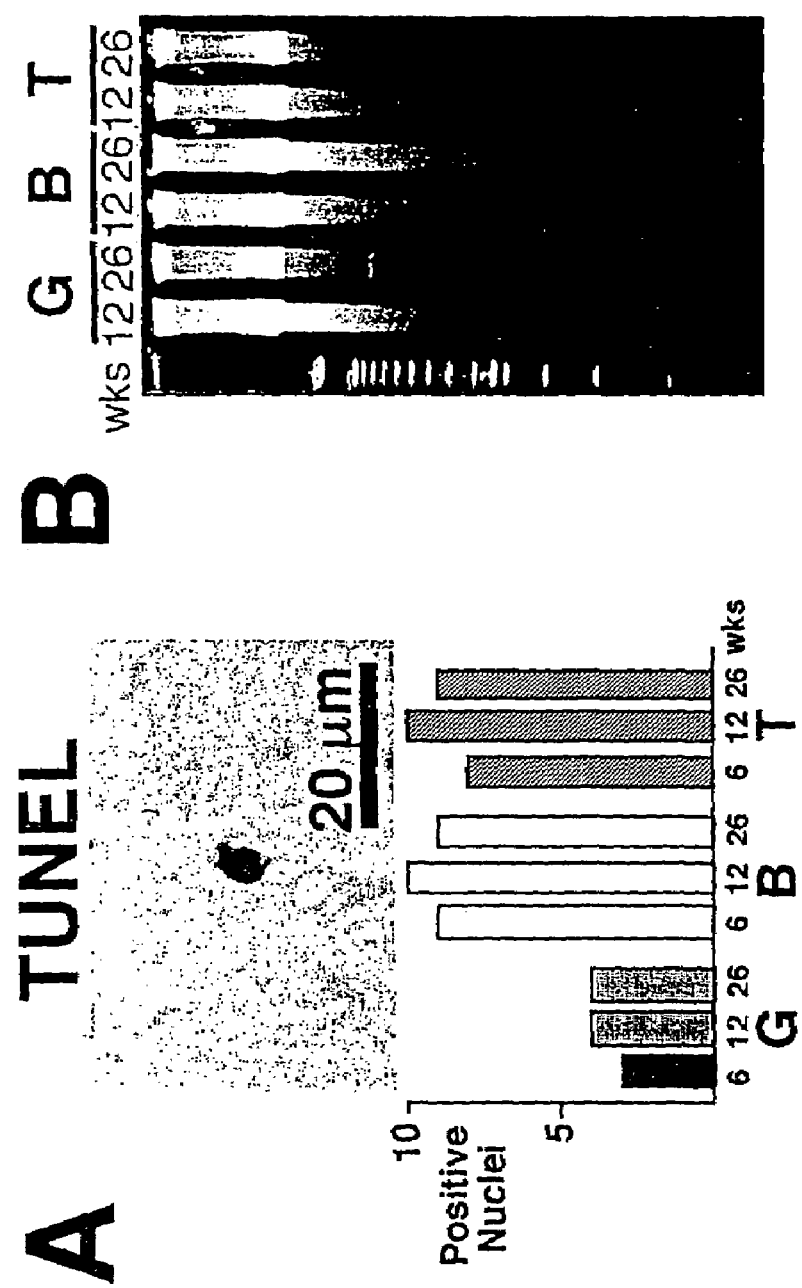
FIG. 3 is a photograph as a drawing which shows the result of investigation of apoptosis in normal hamster and cardiomyopathic hamster. G in FIG. 3 shows a normal Golden hamster, B shows a hypertrophic cardiomyopathic BIO 14.6 hamster and T shows a dilated cardiomyopathic TO-2 hamster. (A) in FIG. 3 shows TUNEL-positive cell numbers in the cross section of the heart and (B) shows electrophoresis of genomic DNA extracted from cardiac muscle.

Next, from a pathological viewpoint, apoptosis and necrosis of cardiac muscle cells were investigated. Firstly, the number of TUNEL (TdT-mediated X-dUTP nick end labeling)-positive cells in the cross section of heart and the laddering of genomic DNA were investigated. The result is shown in FIG. 3 by a photograph as a drawing. (A) in the left of FIG. 3 shows the result of investigation with reference to the number of TUNEL-positive cells in the cross section of hearts of hamsters G, B and T of 6, 12 and 26 weeks of age. (B) in the right of FIG. 3 shows the result of investigation with reference to electrophoresis of genomic DNA extracted from cardiac muscle of hamsters G, B and T of 12 and 26 weeks of age.

As a result, the number of TUNEL-positive cells in both B and T was rather large, however, there were no significant difference between them. With reference to the laddering of genomic DNA, the DNA ladder of 180 bp units specific to apoptosis was not detected in any one of BIO 14.6 and TO-2.

Figure 4:
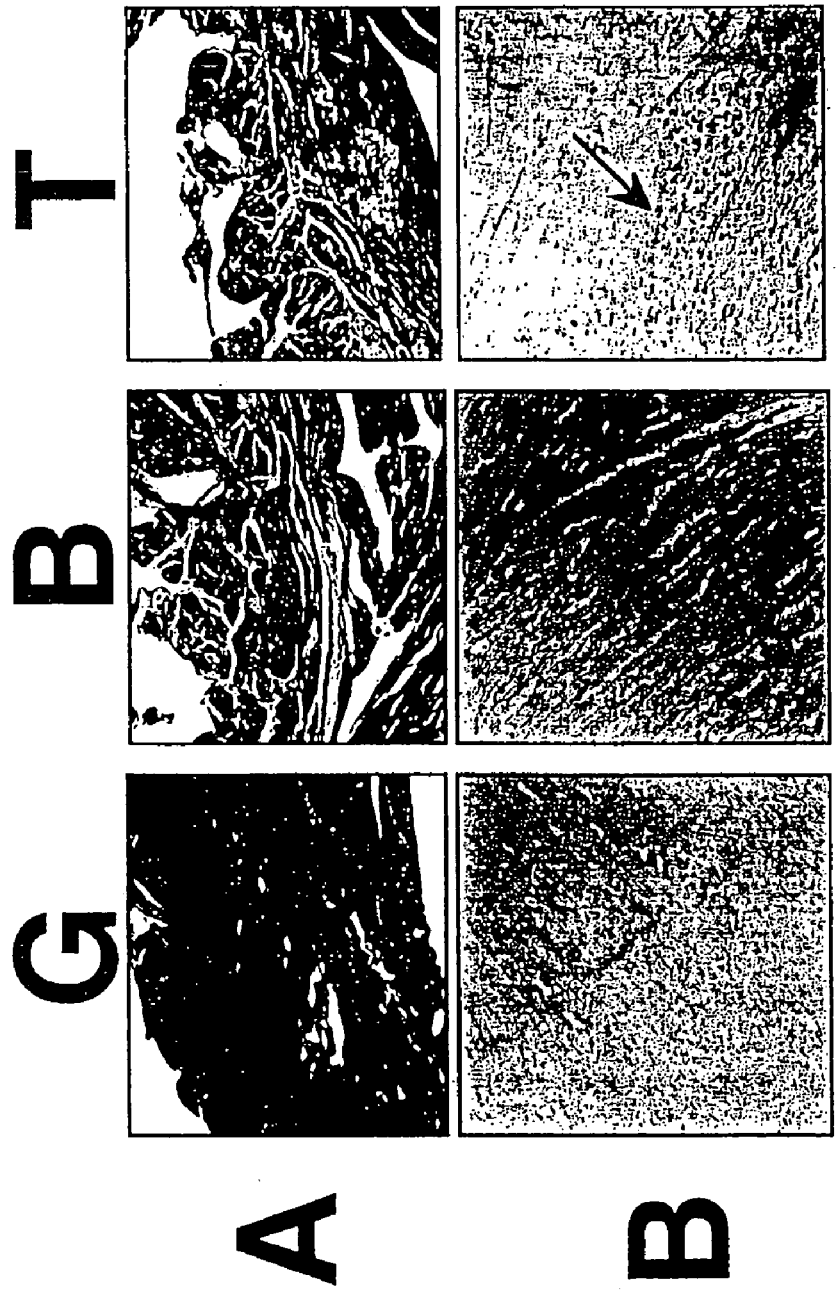
FIG. 4 is a photograph as a drawing which shows the result of investigation of necrosis in normal hamster and cardiomyopathic hamster. G in FIG. 4 shows a normal Golden hamster, B shows a hypertrophic cardiomyopathic BIO 14.6 hamster and T shows a dilated cardiomyopathic TO-2 hamster. (A) in FIG. 4 shows the case of Masson trichrome stain and (B) shows the case of toluidine blue stain. An arrow in TO-2 shows the area where inflammatory cellular infiltration is severe. All the test animals are 26 weeks after birth.

Investigation for necrosis was performed using hamsters of 26 weeks of age stained with Masson trichrome and toluidine blue. The result is shown in FIG. 4 by a photograph as a drawing. G in the left hand side of FIG. 4 is a normal Golden hamster, B in the middle is a hypertrophic cardiomyopathic BIO 14.6 hamster and T in the right hand side is a dilated cardiomyopathic TO-2 hamster. (A) in the upper row of FIG. 4 shows the result of Masson trichrome stain and (B) in the lower row of FIG. 4 shows the result of toluidine blue stain.

Consequently, the severe fibrosis (stained in blue; FIG. 4(A)) and inflammatory cell infiltration (with an arrow FIG. 4(B) ) were found in TO-2.

Fibrosis and inflammatory cell infiltration being severe in T (FIG. 4), it was confirmed that the degeneration of cardiac muscle has been caused not by apoptosis but necrosis.

Figure 5:
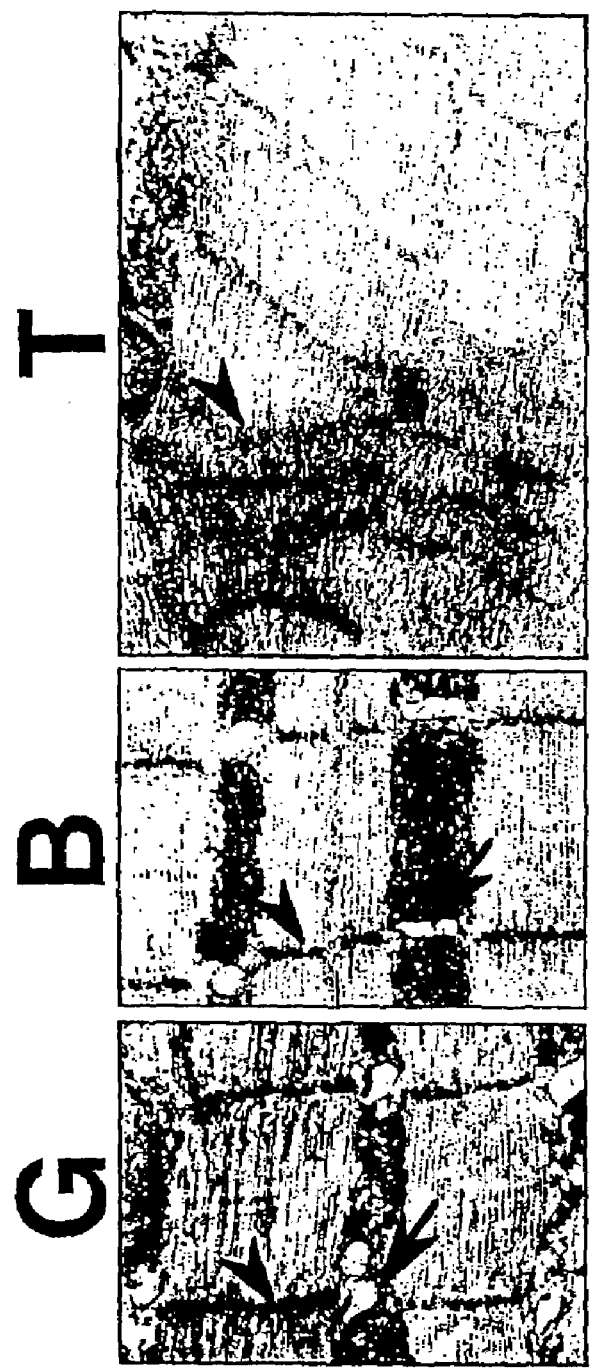
FIG. 5 is a photograph as a drawing which shows the transmission electron microscopic image of left ventricle of normal hamster and cardiomyopathic hamster. G in FIG. 5 shows a normal Golden hamster, B shows a hypertrophic cardiomyopathic BIO 14.6 hamster and T shows a dilated cardiomyopathic TO-2 hamster. An arrow head in TO-2 shows a Z-line which became thinner and an arrow shows a T-tubule. All the test animals are 14 weeks after birth.
Figure 6:
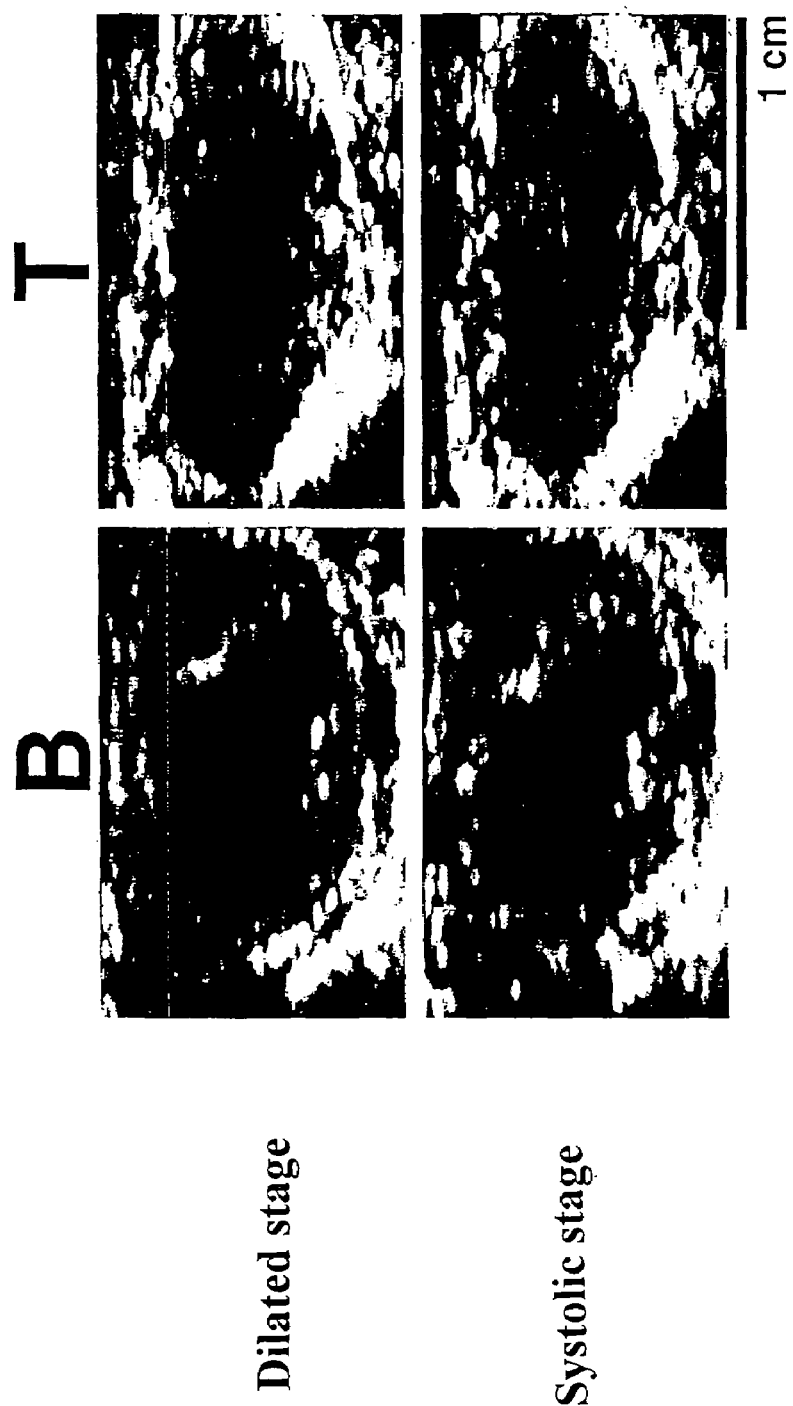
FIG. 6 is a photograph as a drawing which shows ultrasonic imaging diagnosis of the heart of cardiomyopathic hamster. B in FIG. 6 shows a hypertrophic cardiomyopathic BIO 14.6 hamster and T shows a dilated cardiomyopathic TO-2 hamster. The upper row of FIG. 6 is an image at dilated stage and the lower row is an image at systolic stage. All the test animals are 26 weeks after birth.

Further, pathology of those hamsters has been observed under transmission electron microscope (TEM) and ultrasonic imaging diagnosis. Result of the observation under the transmission electron microscope is shown in FIG. 5 by a photograph as a drawing while result of the observation by ultrasonic imaging diagnosis is shown in FIG. 6 by a photograph as a drawing. G in the left hand side of FIG. 5 is a normal Golden hamster, B in the middle is a hypertrophic cardiomyopathic BIO 14.6 hamster and T in the right hand side is a dilated cardiomyopathic TO-2 hamster. B in the left hand side of FIG. 6 is a hypertrophic cardiomyopathic BIO 14.6 hamster and T in the right hand side is a dilated cardiomyopathic TO-2 hamster.

Three morphological abnormalities were found in the left ventricle muscle of TO-2: (1) Z-line (shown by arrow head) corresponding to striation of myofibril is thin and partially cleaved; (2) T-tubules are reduced in number (shown by arrow) (3) some uneven intervals are found in between the Z-lines (refer to FIG. 5). Contrary to the ventricular wall of BIO14.6 which contracts concentrically, it was further found as a result of the ultrasonic imaging diagnosis that the ventricle wall of TO-2 was not only merely thin but the motion thereof was non-cooperative across the ventricle showing spatial disorder (refer to FIG. 6).

Figure 7:
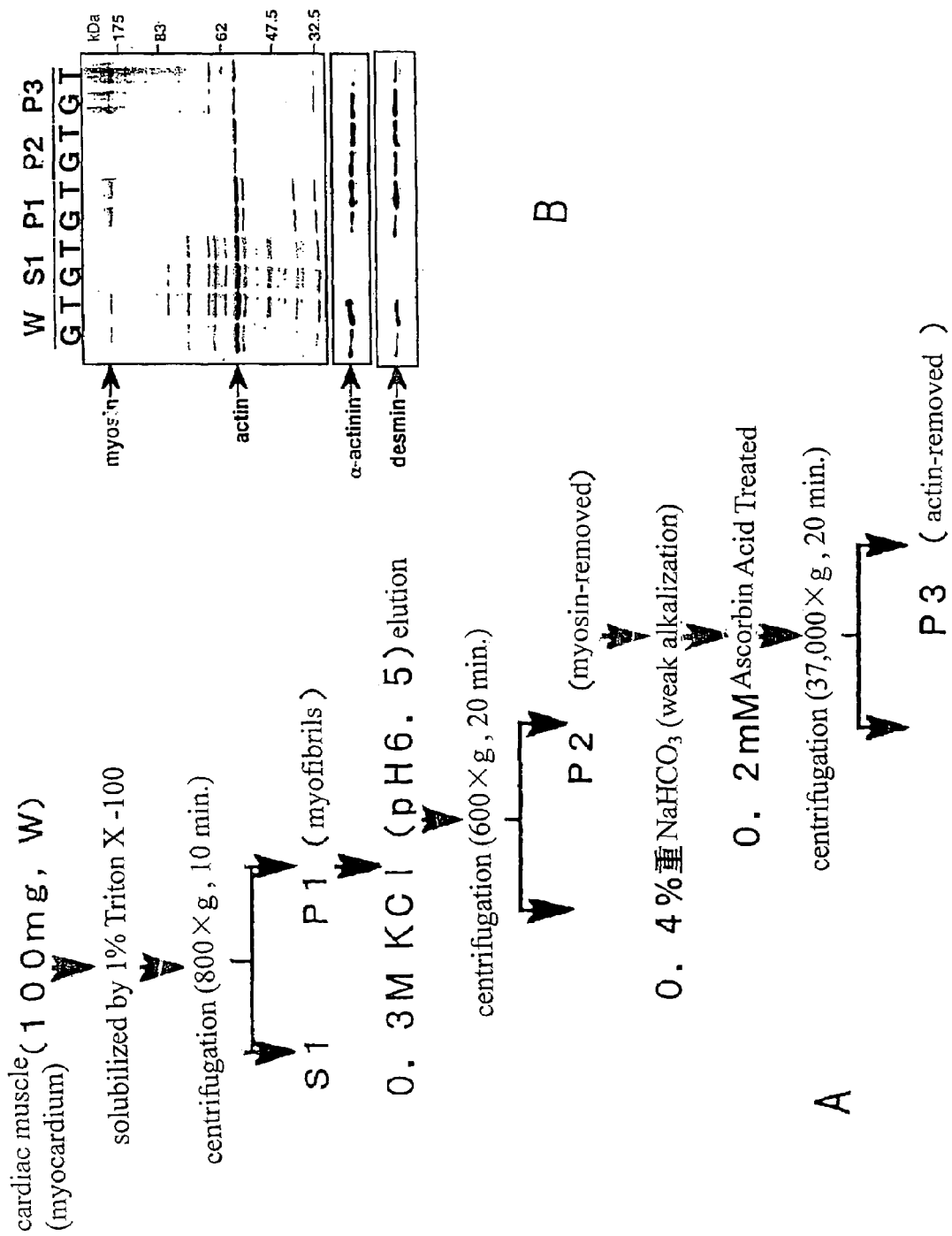
FIG. 7 is a drawing which shows a stepwise purification process of myocardial myofibrils and a photograph as a drawing which shows the result of investigation regarding a behavior of Z-line protein in normal hamster and dilated cardiomyopathic hamster. G in FIG. 7 shows a normal Golden hamster and T shows a dilated cardiomyopathic TO-2 hamster. (A) in FIG. 7 shows a purification protocol and each purification stage is indicated as W, S1, P1, P2, P3, respectively. (B) shows the result of SDS-PAGE with CBB stain (upper row) and immunoblot (lower row) at each purification stage. The animals are six weeks after birth.

From the above, it was observed that Z-line of cardiac muscle in T was thin and partially cleaved, showing abnormality present in Z-line protein of T. Myofibril was extracted from the left ventricle of the hamster of 6 weeks after birth, wherefrom myosin and actin were removed stepwise according to the purification protocol (FIG. 7 in the left hand side), thereby prepared a specimen of concentrated Z-line protein. Then the presence or absence of α-actinin and desmin, those which are known Z-line proteins, was traced by immunoblot analysis. FIG. 7 in the right hand side is a photograph as a drawing which shows the result of SDS-PAGE with CBB stain (upper row) and the immunoblot (lower row) of normal Golden hamster (G) and TO-2 (T) at each concentration step of Z-line protein, wherein W is a whole homogenate of cardiac muscle; P1 is a fraction of myofibrils solubilized with a surfactant; S1 is a fraction other than P1; P2 is a fraction obtained by removal of myosin from P1; P3 is a fraction obtained by removal of actin from P2.

Figure 8:
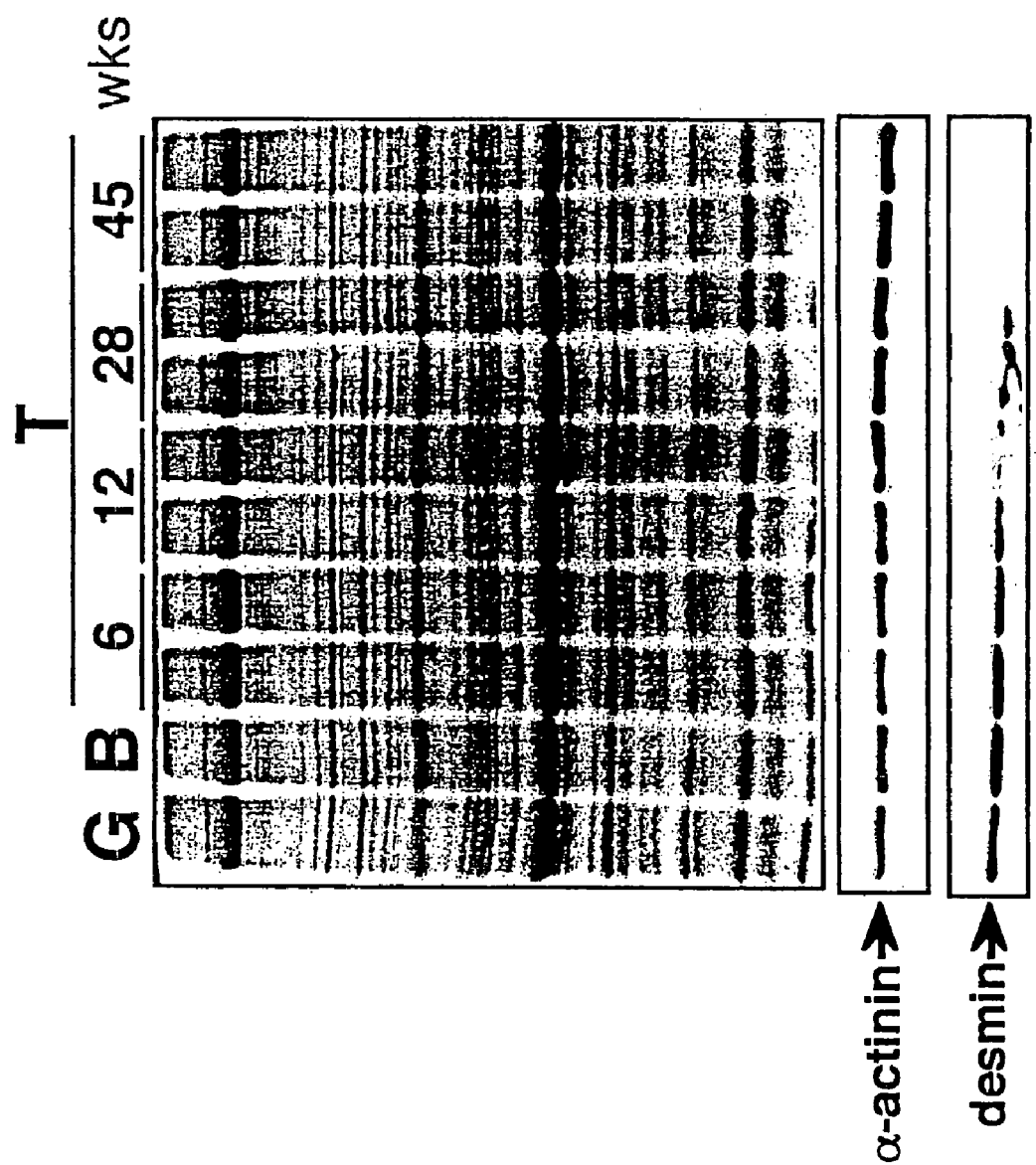
FIG. 8 is a photograph as a drawing which shows the result of investigation into the deformation of Z-line protein with aging in normal hamster and cardiomyopathic hamster. G in FIG. 8 shows a normal Golden hamster, B shows a hypertrophic cardiomyopathic BIO 14.6 hamster and T shows a dilated cardiomyopathic TO-2 hamster. SDS-PAGE with CBB stain (upper row) and immunoblot (lower row) of whole cardiac muscle homogenate are shown.

In regard to the detection of both α-actinin and desmin, no change has been observed between hamster T (6 weeks after birth) and G at those stages of the whole homogenate, the myofibril fraction and the myofibril fraction after removal of myosin, while detected a significant decrease in both α-actinin and desmin at the stage after the removal of actin (refer to FIG. 7). Actin being a protein which binds to Z-line, removal thereof is artificial destabilization of Z-line. The resulting significant decrease in α-actinin and desmin warns a structural disruption of Z-line in T, and that agrees with the observation under a TEM. Cardiac muscle continues to contract till one dies so that the mechanical stress caused thereby accumulates with aging. Further investigation has been conducted for the changes of α-actinin and desmin with aging in regard to the whole homogenate of left ventricle from G, B and T (6, 12, 28 and 45 weeks of age). The result is shown in FIG. 8 by a photograph as a drawing. Upper row in FIG. 8 shows a photograph of SDS-PAGE with CBB stain, lower row shows a photograph of immunoblot. Consequently, desmin in T has been gradually decreased in the amount with aging, while no changes has been observed with α-actinin. It was found through the above investigations that the Z-line protein in T, particularly desmin, was quite unstable.

Desmin has been known as an intermediate filament protein located in Z-line domain of skeletal muscle or cardiac muscle and of which genetic abnormality causes the cardiomyopathy complicated with muscular dystrophy (Goebel, H. H., et al., *Muscle & Nerve*, 18: 1306-1320, 1995). With regard to an animal model thereof, the so-called knock out mouse with complete disruption of desmin gene has been prepared by two respective groups (Milner, D. J., et al., *J. Cell Biol.*, 134: 1255-1270, 1996; Li, Z., et al., *Dev. Biol.*, 175: 362-366, 1996).

Incidentally, with regard to the human cardiomyopathy resulting from the abnormality of desmin gene reported so far is caused by a point mutation thereof in all cases, whereas no case with complete loss of desmin gene has been reported. In such a case, desmin protein, though existing in infant period, gradually disappears from the Z-line domain with aging, thereby results in onset of cardiomyopathy. Contrary to the above, in the desmin knockout mice that lack desmin protein completely upon birth, onset of cardiomyopathy as well as the occurrence of the destruction of fine structures of cardiac or skeletal muscle cells such as myofibrils and mitochondria are immediate. Owing to the above, the desmin knockout mouse has been considered to be unappropriate for the development of novel therapeutic method for preventing cardiomyopathy before its onset due to the difficulties in tracing the time course of changes of disintegration of cardiac muscle cell resulting from the abnormality of desmin gene.

Desmin gene and cDNA per se of Syrian hamster have already been isolated (Quax, W., et al., *Cell*, 1985: 43(1): 327-38) and have been employed in the studies relating to the gene expression regulation and the formulation of protein complexes. However, they have never been used for studies in terms of cause and significance of the onset mechanism of hereditary cardiomyopathy in hamsters.

Figure 9:
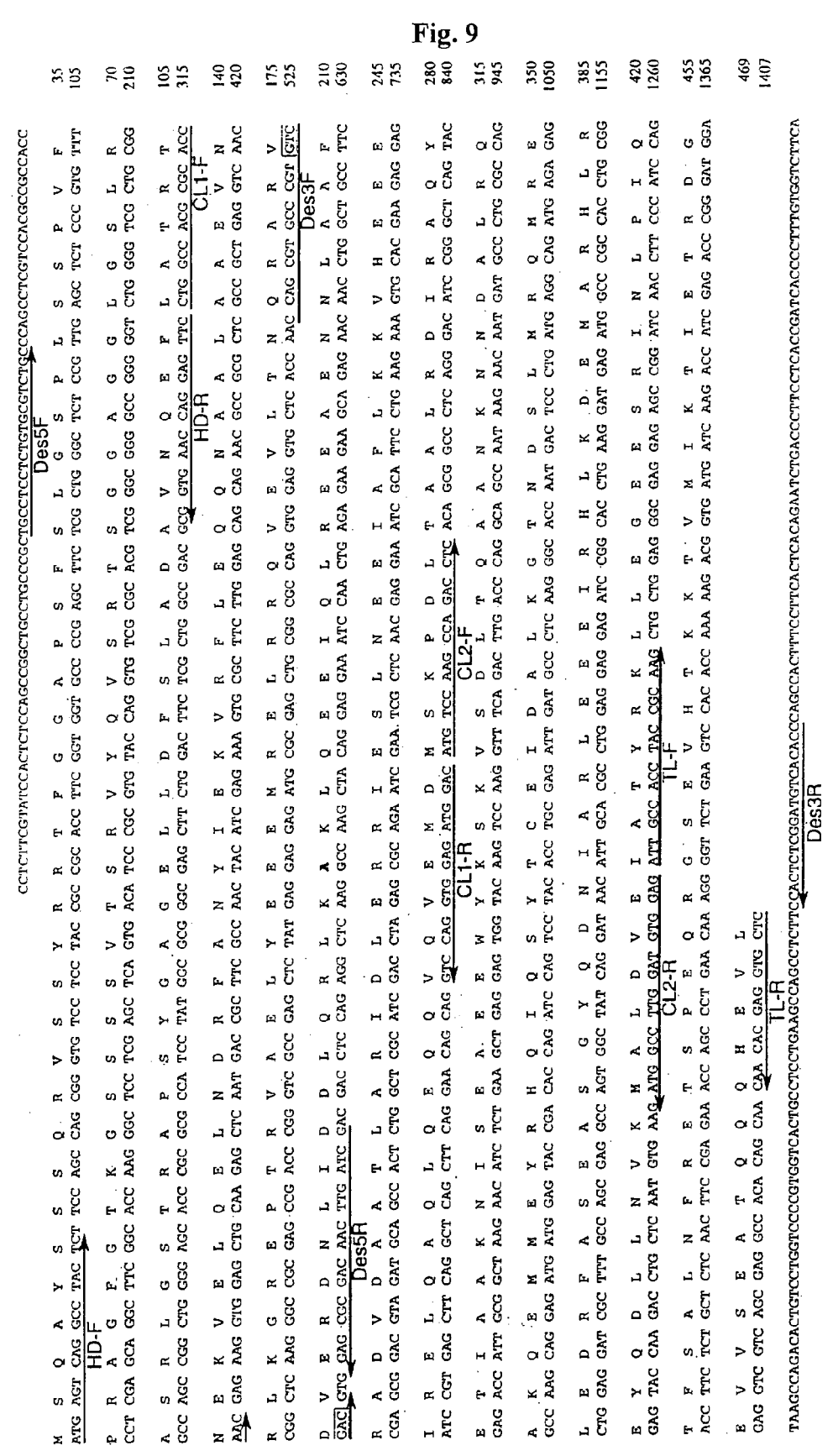

RT-PCR primer sets (Des5F/Des5R and Des3F/Des3R as shown in FIG. 9) to amplify the complete ORF (open reading frame) and a reaction condition have been established from the disclosed base sequence of desmin cDNAs of Syrian hamster. Then desmin cDNAs of G and T were cloned and the base sequences thereof were determined. The ORF (open reading frame) of desmin gene of G comprises 1407 bases and has been considered to encode a polypeptide of molecular weight of 53,445 comprising 469 amino acid residues. As a result of computer analysis of the amino acid sequences (Lupas, A., van Dyke, M. and Stock, J. (1991), "Predicting Coled Coils from Protein Sequences", *Science*, 252: 1162-1164, http://www.ch.embnet.org/software/COILS_form.html), it has been predicted that desmin is a protein having a coiled-coil structure comprising an amino-terminal head domain, coiled-coil dimmer of a central domain and a carboxyl-terminal tail domain (refer to FIG. 14(A)).

FIG. 9 shows a base sequence of desmin cDNA of Syrian hamster. The translated amino acid is shown by one-letter code above the corresponding codon. The allotted base numbers cover only the translated region of the sequence. Desmin cDNA which covers the whole translated region can be obtained by ligating RT-PCR products prepared with Des5F/Des5R and Des3F/Des3R primers shown in FIG. 9 at a recognition site of restriction endonuclease (Sal I) marked by box (refer to FIG. 12). The primers for amplification of four domains (refer to FIG. 14) of desmin were clearly indicated by arrows as well.

Figure 12:
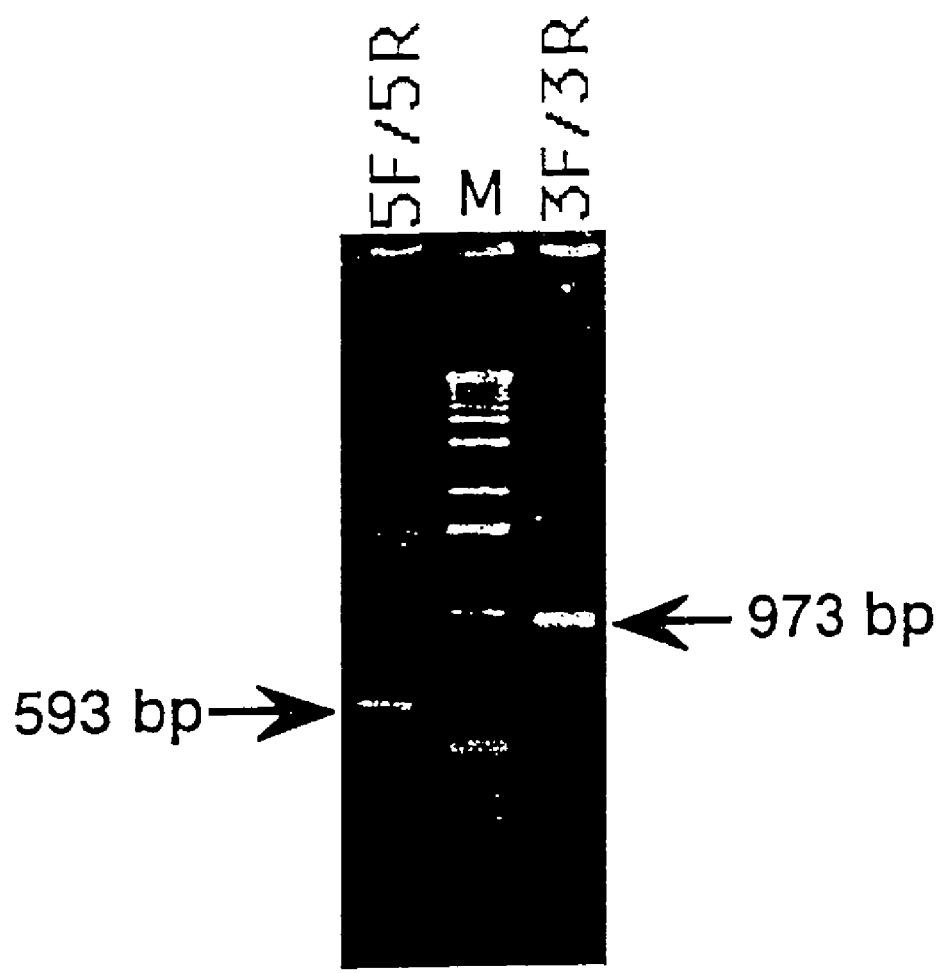
FIG. 12 is a photograph as a drawing which shows the result of a PCR carried out with two primer sets (Des5F/Des5R and Des3F/Des3R) using cDNA synthesized from left ventricle muscle of normal Golden hamster as a template. M shows a marker.

FIG. 12 is a photograph as a drawing which shows the result of PCR carried out with two sets of primer (Des5F/Des5R and Des3F/Des3R) shown in FIG. 9 by using cDNA synthesized from the left ventricle muscle of Golden hamster as a template. M is a marker. Consequently, it is noted that 593 bp PCR product was prepared by PCR with a primer set of Des5F/Des5R, while 973 bp of PCR product was prepared by PCR with a primer set of Des3F/Des3R.

Through determination of base sequence as a consequence of the cloning of desmin cDNA of hamster T, it has been noted a point mutation (G571A) in T located in coil-1 and converts the 191st alanine preserved in all known species to threonine. No such a base mutation has been observed in BIO 14.6 hamster. The secondary gene abnormality in TO-2 is considered to be a missense mutation of desmin gene which is the constituents of the Z-line.

FIG. 13 shows a base mutation of genome in a dilated cardiomyopathic hamster TO-2 and detection thereof by a PCR. FIG. 13(A) shows base sequences of genome adjacent to the point mutation (G571A) site of desmin gene in Golden and TO-2 hamsters, wherein the bases identical in both sequences are indicated by dots (.). Base sequences in the first exon and in the first intron are indicated by uppercase and lowercase respectively. Base numbers correspond to those in the cDNA sequence of FIG. 9. Examples of the primers used for genetic diagnosis are shown by arrows. FIG. 13(B) is a photograph as a drawing which shows the result of genomic PCR using a primer set (DesF/DesGR) or (DesF/DesTR). It is noted that the 571st base of desmin amplifies the band specific to G or A, respectively. It has also been noted that the alleles in Golden, BIO 14.6 and TO-2 are (G/G), (G/G) and (A/A).

Figure 14:
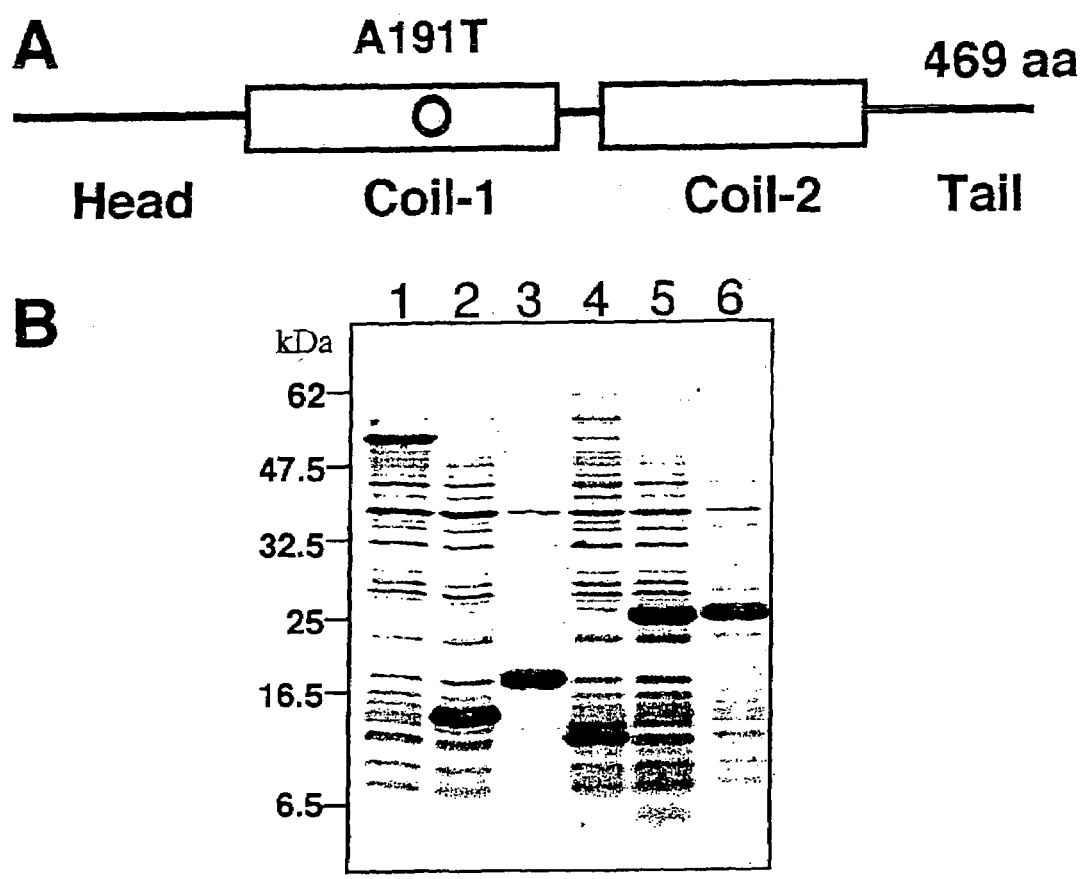
FIG. 14 is a drawing which shows molecular structure of desmin and a photograph as a drawing which shows the expression of recombinant protein in each domain.

The molecular structure of desmin and the result of expression of recombinant protein of each domain are shown in FIG. 14 by a photograph as a drawing. FIG. 14(A) schematically shows the molecular structure of desmin. The amino acid mutation (marked with ○ in FIG. 14(A)) in TO-2 resides in coil-1 rod segment. FIG. 14(B) is a photograph as a drawing showing full length desmin and recombinant proteins for each domain. cDNA of each domain was amplified with primer sets of FIG. 1, inserted into expression vector pET33b and expressed in *Escherichia coli* BL21 (DE3). The photograph shows the result that the whole lysate of each *Escherichia coli* was subjected to SDS-PAGE and stained with CBB. The bands corresponding to the aimed proteins are marked with asterisks (*). Lane 1 shows the result of full-length desmin, lane 2 shows the result of head domain, lane 3 shows the result of coil-2 segment, lane 4 shows the result of tail domain, lane 5 shows the result of a normal coil-1 (191A) and lane 6 shows the result of a mutant coil-1 (191T).

A point mutation (G571A) is present in desmin of TO-2 (refer to FIG. 13), therefore the 191st amino acid normal A (alanine) has been altered to T (threonine). The base sequence of desmin of TO-2 with a point mutation is represented by SEQ ID NO: 1 in the Sequence Listing, while the corresponding amino acid sequence of the translated region thereof is represented by SEQ ID NO: 2.

Then, in order to clarify the function of desmin, the linkage mechanism of sarcoplasmic membrane and myofibril of cardiac muscle have been investigated.

Figure 10:
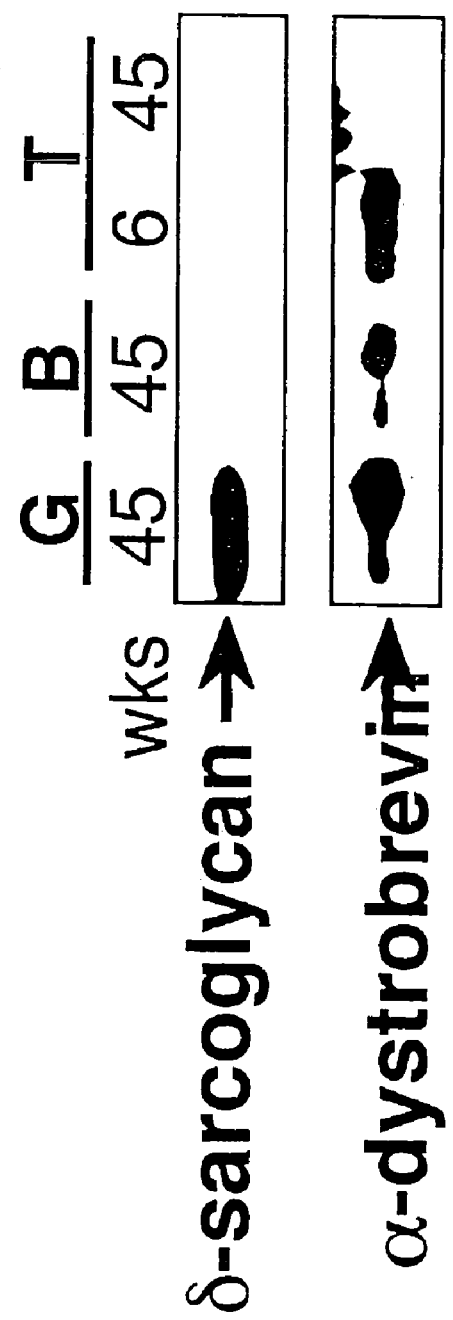
FIG. 10 is a photograph as a drawing which shows the result of investigation regarding the specific disappearance of α-dystrobrevin in cardiomyopathic hamster TO-2. G in FIG. 10 shows a normal Golden hamster, B shows a hypertrophic cardiomyopathic BIO 14.6 hamster and T shows a dilated cardiomyopathic TO-2 hamster. The result of immunoblot using whole cardiac muscle homogenate is shown. The upper row in FIG. 10 shows δ-sarcoglycan and the lower row shows α-dystrobrevin.

By immunostain of isolated cardiac muscle cells, present inventors have firstly revealed that α-dystrobrevin, which is a dystrophin-associated protein generally present in T-tubules in the cardiac muscle, was hardly observed in T of 45 weeks of age, but observed in a normal hamster (G). The result of immunoblot using the whole homogenate of cardiac muscle is shown in FIG. 10 by a photograph as a drawing. The deficiency of a-dystrobrevin, independent of the deficiency of δ-sarcoglycan which is the causative gene common in cardiomyopathic hamster, was specific to TO-2 of 45 weeks of age where desmin has been deleted.

Figure 11:
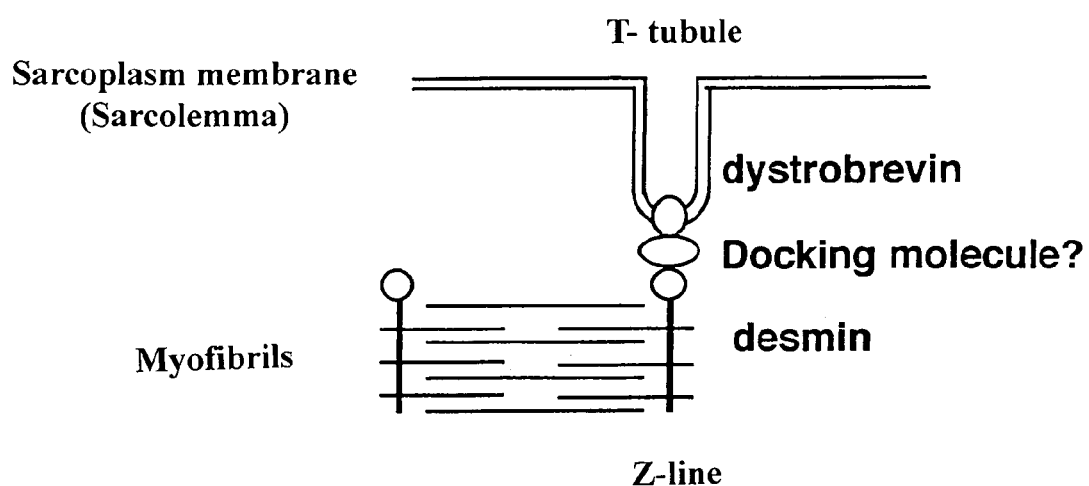
FIG. 11 schematically shows a linkage model of sarcoplasmic membrane with myofibril in T-tubule region. The linkage of α-dystrobrevin and desmin may be direct, or indirect mediated by some docking molecule as shown in FIG. 11.

Judging from the above results together with the observation under TEM i.e. T-tubules being hardly found in hamster T, it is presumed that the linkage mechanism between sarcoplasmic membrane and myofibrils in the cardiac muscles is closely related to the bond, whichever direct or indirect, of α-dystrobrevin in T-tubules and desmin on Z-line. Such a structure is schematically shown in FIG. 11. FIG. 11 showing a linkage model of sarcoplasmic membrane and myofibrils assumed from the above description, it seems that the linkage mechanism of cardiac sarcoplasmic membrane and myofibril via α-dystrobrevin and desmin propagates the electrical excitation over sarcoplasmic membrane into myofibrils, and reversely transmits the tension within myofibrils to sarcoplasmic membrane. Though not revealed at present whether the bond between α-dystrobrevin and desmin is direct or indirectly mediated by a certain docking molecule, it has been made clear that those molecules are somewhat interacting.

In hamster T, it is clearly understood that the spatially nonuniform contraction detected in the cardiac muscle cells (TEM photo images; FIG. 5) or in a whole heart (ultrasonic imaging diagnosis; FIG. 6) has been caused by nonuniform propagation of electrical excitation from sarcoplasmic membrane to myofibrils resulted from the structural defect in T-tubules due to the abnormality of desmin gene.

As such, the secondary causative gene for cardiomyopathy within TO-2 has been clarified by the present invention. Moreover, the functional significance of desmin as a binder for the linkage between T-tubule and myofibril has been revealed by the present invention for the first time in the world.

The present invention has ascertained one of the causes for hereditary cardiomyopathy as a point mutation of desmin gene relating to T-tubule of cardiac muscle. The location of point mutation in the present invention is the site corresponding to the 571-position of the base sequence in the desmin cDNA translated region of Syrian hamster, however, it is not always limited to such a site but may vary depending on the animals to use. For example in the case of human desmin, "what position of desmin cDNA translated region corresponds to the point mutation site" has to be determined with good consideration of homology of amino acid sequence, configuration of peptide and so on. Accordingly, "the site corresponding to the 571-position of the base sequence in the desmin cDNA translated region of Syrian hamster" in the present invention means that it corresponds to a position performing the same function as the peptide function of desmin and a position determined in accordance with desmin's amino acid sequence homology, peptide configuration, etc. depending upon types of animals.

The present invention has clarified that the point mutation in Syrian hamster is an alteration from G to A, however, the invention is not limited only to such a mutation. The important thing in the present invention is that cardiomyopathy occurs resulting from the point mutation at that site, and the present invention intends to include the varied gene mutations depending upon types of animals.

As for the specific example in Syrian hamster, a base sequence of SEQ ID NO:1 of the Sequence Listing is shown, where translation starts from the site corresponding to the 82-position meaning that the location of the point mutation is shown at the site corresponding to the 652-position. In the inherent desmin, the sequence of bases 652-654 is "gcc" encoding alanine, while the gene of the present invention is altered to "acc" encoding threonine as a result of the point mutation.

The present invention is to clarify the occurrence of hereditary cardiomyopathy due to a point mutation in the desmin gene. It is possible to judge whether or not it is a causative gene of the hereditary cardiomyopathy by detecting and identifying the point mutation "at the site corresponding to the 571-position of the base sequence in the desmin cDNA translated region of Syrian hamster". As for a test substance, genome of animals such as human being, mouse, hamster and rat can be used.

With regard to the method for detection and identification of the present invention, any methods generally used for detecting and identifying genes can be utilized. For example, it is possible to detect and identify the presence of point mutation by amplifying gene containing a point mutation with the method such as PCR using base sequences in the vicinity of the point mutation, followed by examining the presence of amplification or analyzing the amplified genes. Examples of the preferred primer sets for PCR are the combination of a forward primer having the base sequence of SEQ ID NO: 9 with a reverse primer having a base sequence of SEQ ID NO: 10, a reverse primer having a base sequence of SEQ ID NO: 11 or a reverse primer having a base sequence of SEQ ID NO: 12.

It is also possible to detect and identify the point mutation of the present invention using DNA chip where oligonucleotides containing the point mutation is immobilized by the same method as used for detecting and identifying SNP of genome.

The present invention is to provide oligonucleotides with 5 to 250 bases comprising "the site corresponding to the 571-position of the base sequence in the desmin cDNA translated region of Syrian hamster" or oligonucleotides comprising the complementary sequence thereto. The oligonucleotides of the present invention can be used for detecting and identifying the point mutation in the present invention. With regard to the length of the oligonucleotides of the present invention, any length sufficient for use of detection and identification is acceptable, examples of length of oligonucleotides are 5 to 250 bases, 5 to 150 bases, 5 to 50 bases, 5 to 30 bases, 5 to 20 bases or 7 to 250 bases, 7 to 150 bases, 7 to 50 bases, 7 to 30 bases, 7 to 20 bases, further, 10 to 250 bases, 10 to 150 bases, 10 to 50 bases, 10 to 30 bases, 10 to 20 bases, etc., they may be used depending upon the objects.

The oligonucleotides of the present invention may be used as a primer or a probe. When used as a probe, it may be labeled or immobilized on a carrier same as DNA chip.

Further, the present invention is to provide a kit for detecting and identifying the point mutation "at the site corresponding to the 571-position of the base sequence in the desmin cDNA translated region of Syrian hamster". With regard to such a kit, it is possible to utilize a kit generally used for detecting and identifying genes. When it is used for detection and identification by means of amplification with a method such as PCR, the kit includes a primer set for the amplification, reagents for amplification treatment, reagents for detecting and identifying the amplified products, etc. For the case such as DNA chip, the kit includes DNA chip on which immobilized the oligonucleotides for detecting and identifying a point mutation, reagents for treatment thereof, and so on.

By using the kit of the present invention, it is possible to judge whether or not the gene is causative of hereditary cardiomyopathy.

The present invention is to provide a primer set for amplifying each domain of the desmin gene. As shown in FIG. 14, desmin being a polypeptide comprising head domain, coil-1 domain, coil-2 domain and tail domain, there provided primer set(s) for amplifying one of the above domains, or, two or more of successive domains. To be more specific, as shown in FIG. 9, with regard to a primer set for amplifying the head domain, it can be used HD-F (SEQ ID NO: 13 of the Sequence Listing) as a forward primer and HD-R (SEQ ID NO: 14 of the Sequence Listing) as a reverse primer; with regard to a primer set for amplifying the coil-1 domain, it can be used CL1-F (SEQ ID NO: 15 of the Sequence Listing) as a forward primer and CL1-R (SEQ ID NO: 16 of the Sequence Listing) as a reverse primer; with regard to a primer set for amplifying the coil-2 domain, it can be used CL2-F (SEQ ID NO: 17 of the Sequence Listing) as a forward primer and CL2-R (SEQ ID NO: 18 of the Sequence Listing) as a reverse primer; and with regard to a primer set for amplifying the tail domain, it can be used TL-F (SEQ ID NO: 19 of the Sequence Listing) as a forward primer and TL-R (SEQ ID NO: 20 of the Sequence Listing) as a reverse primer. Simultaneous amplifications of two or more successive domains are also possible by appropriately combining those primers.

With regard to a primer set for amplifying the 5'-terminal domain of desmin, it can be used Des5F (SEQ ID NO: 5 of the Sequence Listing) as a forward primer and Des5R (SEQ ID NO: 6 of the Sequence Listing) as a reverse primer; with regard to a primer set for amplifying the 3'-terminal domain of desmin, it can be used Des3F (SEQ ID NO: 7 of the Sequence Listing) as a forward primer and Des3R (SEQ ID NO: 8 of the Sequence Listing) as a reverse primer.

With regard to a primer set for amplifying the domain including a point mutation, it can be used DesF (SEQ ID NO: 9 of the Sequence Listing) as a forward primer and DesGR (SEQ ID NO: 10 of the Sequence Listing) as a reverse primer; with regard to a primer set for specifically amplifying the point mutation site, it can be used DesF (SEQ ID NO: 9 of the Sequence Listing) as a forward primer and DesTR (SEQ ID NO: 12 of the Sequence Listing) or shorter primer of DesTR (SEQ ID NO: 11 of the Sequence Listing) as a reverse primer.

The present invention is to provide those primer sets.

The present invention is to provide desmin encoded by the desmin gene having a point mutation "at the site corresponding to the 571-position of the base sequence in the desmin cDNA translated region of Syrian hamster". Examples of desmin encoded by the desmin gene of the present invention having a point mutation includes polypeptides prepared from animals such as hamster, human being, mouse and rat. The desmin encoded by the desmin gene of the present invention having a point mutation is a polypeptide not only useful for a functional and structural analysis with regard to the striated muscle such as cardiac muscle but also useful for a clarification of neurotransmission mechanism in T-tubules, and so forth. A specific example for desmin encoded by the desmin gene of the present invention having a point mutation is the one having an amino acid sequence of SEQ ID NO: 2 in the Sequence Listing. As the above amino acid sequence being one of the examples of the sequences of the polypeptide of the present invention, it is not particularly limited only to said amino acid sequence, but includes the sequence where a part of amino acid are deleted, substituted and added with respect to SEQ ID NO: 2 as long as it has the same functions. In other words, the desmin encoded by the desmin gene of the present invention is a polypeptide having a function of desmin wherein an amino acid having a point mutation is incorporated.

As shown in FIG. 14, the present invention further provides a polypeptide comprising head domain, coil-1 domain, coil-2 domain or tail domain of desmin. The coil-1 domain of desmin includes the point mutation of the present invention, and the present invention is to provide a polypeptide comprising coil-1 domain of desmin where one of alanines in the coil-1 domain is altered to threonine.

The present invention still further provides an antibody against the polypeptide of the present invention. The antibody of the present invention may be a polyclonal antibody or a monoclonal antibody. The antibody of the present invention may be produced using the above-mentioned polypeptide of the present invention by a common method such as a cell fusion method using animal cells of rat, rabbit or the like subjected to immunization.

The present invention has clarified that the point mutation at the specific site of desmin gene is a cause of hereditary cardiomyopathy. It is now possible to produce an animal model for disease having a genetic abnormality using a desmin gene having point mutation "at the site corresponding to the 571-position of the base sequence in the desmin cDNA translated region of Syrian hamster". An animal model for disease of the present invention includes various kinds of animals except for human being, without any particular limitation, examples of which are such as mouse, hamster, rat, chicken, rabbit and dog. An animal model for disease of the present invention may be produced by using a gene having a point mutation of the present invention employing genetic engineering technique such as gene targeting using ES cell or fertilized egg. When the animal model for disease is hamster, it can be produced by subjecting TO-2 hamster to crossbreeding with other normal hamster.

For example, TO-2 hamster is crossbred with Golden hamster and genome DNA is extracted from concha of its offspring. In such an offspring, there may be detected the deficiency of δ-sarcoglycan gene and the point mutation of desmin gene carried from TO-2 . The former is subjected to a gene diagnosis by a method which has already been developed by the present inventors (Sakamoto, A., et al., *FEBS Lett.*, 1999, 447, 124-128), while the latter is subjected to a gene diagnosis by a method disclosed in the present invention. δ-sarcoglycan gene gives male and female animals which are normal homo while desmin gene gives those which are abnormal homo, whereupon congenic strains are established finally.

Such a novel animal model for genetic cardiomyopathy, presumably slow in onset, can be expected to be useful as an animal model for human cardiomyopathy caused by the abnormality of desmin gene. Specific applications are shown below.

(a) It is useful as an animal model for the development of a novel therapeutic method to be applied previously to the onset of human cardiomyopathy resulting from the abnormality of desmin gene.

(b) Diverse expressions of various kinds of genes (refer to FIG. 2) to adapt the myocardial degeneration are observed in ventricular muscle of TO-2 . Accordingly, myocardial samples from TO-2 and from the animals created by the above method are useful for isolation of the novel functional genes by a method such as a differential display method, where the difference in the amount of gene expressions from the normal myocardium is used as an index.

(c) It is useful for follow-up investigation for the time course correlation between degradation of desmin protein and structural disruption of T-tubules.

The present invention further provides a method for preventing and treating the hereditary cardiomyopathy or a method for the screening of a preventive and therapeutic agent using such an animal model for disease. Abnormality residing only in desmin in such an animal model for disease; desmin being clarified as a polypeptide detected commonly in striated muscle and playing an important role for supporting the structure of T-tubules via the bond with a-dystrobrevin as shown in FIG. 10 and FIG. 11, an animal model for disease is useful for revealing the cause of muscular dystrophy or the like relating to the abnormality of striated muscle, and also useful for the development of preventive and therapeutic methods thereof.

As such, in accordance with the present invention, it has been clarified that desmin plays an important role for supporting the structure of T-tubules via the bond with α-dystrobrevin and the protein of each domain of desmin obtained by the method shown in the present specification is quite useful for analysis of various functions of desmin molecule including the ability to support the structure of T-tubules. The contribution to identifying the unknown binding protein is particularly desired.

EXAMPLES

The present invention, though not limited thereto, will now be illustrated in a more specific manner by way of the following Examples.

Example 1

Amplification of Desmin cDNA of Hamster by RT-PCR cDNA was synthesized by a conventional method (Sakamoto, A., et al., *Proc. Natl. Acad. Sci. USA*, 1997: 94(25): 13873-8) from total RNA extracted from left ventricle of Golden and TO-2, respectively.

The PCR was carried out in the following scale using ABI 9700.

| | |
|---|---|
| $H_2O$ | 6.0 μl |
| 10 × buffer | 1.0 μl |
| dNTP (2.5 mM each) | 0.8 μl |
| Forward primer (10 μM) | 0.5 μl |
| Reverse primer (10 μM) | 0.5 μl |
| cDNA | 1.0 μl |
| Advantage 2 (Clontech) | 0.2 μl |
| Total | 10 μl |

A primer set used for the amplification of 5'-side of desmin was as follows.

Des5F: TGC CTC CTC TGT GCG TCT GC    (SEQ ID NO: 5)

Des5R: CGA TCA AGT TGT CGC GCT CC    (SEQ ID NO: 6)

The reaction was carried out under the following conditions:

94° C., 2 min; (94° C., 20 sec; 60° C., 30 sec; 72° C., 1 min)×38 cycles; 4° C.

A primer set used for the amplification of 3'-side of desmin was as follows.

Des3F: CCA GCG TGC CCG TGT CGA CG    (SEQ ID NO: 7)

Des3R: GGT GTG ACA TCC GAG AGT GG    (SEQ ID NO: 8)

The reaction was carried out under the following conditions:

94° C., 2 min; (94° C., 20 sec; 60° C., 30 sec; 72° C., 1 min)×38 cycles; 4° C.

As a result, specific products of 593 bp and 973 bp were amplified, respectively (refer to FIG. 12).

Example 2

Detection of Point Mutation by a Genomic PCR in TO-2 Hamster

Genomic DNA was extracted by a conventional method from tissues (liver, concha, etc.) of hamster and a PCR was carried out according to the following reaction scale using ABI 9700.

| | |
|---|---|
| H₂O | 6.15 µl |
| 10 × buffer | 1.0 µl |
| dNTP (2.5 mM each) | 0.8 µl |
| Forward primer (10 µM) | 0.5 µl |
| Reverse primer (10 µM) | 0.5 µl |
| Genomic cDNA | 1.0 µl |
| Takara Ex Taq | 0.05 µl |
| Total | 10 µl |

A primer set used for the detection of normal allele (571 G) was as follows.

```
DesF:  GAA AGT GCG CTT CTT GGA GC    (SEQ ID NO: 9)

DesGR: GTG CCC TCA CTT GGC           (SEQ ID NO: 10)
```

The reaction was carried out under the following conditions:
94° C., 2 min; (94° C., 20 sec; 67° C., 30 sec; 72° C., 1 min)×35 cycles; 4° C.

A primer set used for the detection of abnormal allele (571 A) was as follows.

```
DesF:   GAA AGT GCG CTT CTT GGA GC   (SEQ ID NO: 9)

DesTR:  CCG TGC CCT CAC TTG GT       (SEQ ID NO: 12)
```

The reaction was carried out under the following conditions: 94° C., 2 min; (94° C., 20 sec; 67° C., 30 sec; 72° C., 1 min)×35 cycles; 4° C.

As a result, products specific to Golden and TO-2 were amplified (refer to FIG. 13), respectively.

Example 3

Amplification and Expression of cDNA Corresponding to Four Structural Domains of Desmin PCR was carried out using ABI 9700 according to the following scale with full-length desmin cDNA of Golden or TO-2 prepared in Example 1 as a template.

| | |
|---|---|
| H₂O | 6.15 µl |
| 10 × buffer | 1.0 µl |
| dNTP (2.5 mM each) | 0.8 µl |
| Forward primer (10 µM) | 0.5 µl |
| Reverse primer (10 µM) | 0.5 µl |
| Full-length desmin cDNA (200 pg/µl) | 1 µl |
| Takara Ex Taq | 0.05 µl |
| Total | 10 µl |

The reaction was carried out under the following conditions:
94° C., 2 min; (94° C., 20 sec; 55° C., 30 sec; 72° C., 1 min)×30 cycles; 4° C.

Primer sets used for amplification of each domain were as follows.

Head domain

```
HD-F:   GGCATATGAGTCAGGCCTACTC       (SEQ ID NO: 13)

HD-R:   CCGAATTCTAGAACTCCTGGTTCACCG  (SEQ ID NO: 14)
```

Coil-1 domain (Coil-1)

```
CL1-F:  GGCATATGCTGGCCACGCGCACCAAC   (SEQ ID NO: 15)

(SEQ ID NO: 16)
CL1-R:  CCGAATTCTAGTCCATCTCCACCTGGAC
```

Coil-2 domain (Coil-2)

```
CL2-F:  GGCATATGTCCAAGCCAGACCTC      (SEQ ID NO: 17)

(SEQ ID NO: 18)
CL2-R:  CCGAATTCTACTCCACATCCAAGGCCATC
```

Tail domain (Tail)

```
TL-F:   GGCATATGATTGCCACCTACCGCAAG   (SEQ ID NO: 19)

TL-R:   CCGAATTCTAGAGCACCTCGTGTTG    (SEQ ID NO: 20)
```

Sequences underlined are specific to the desmin cDNA of hamster. Sequences other than underlined are for insertion into NdeI (CATATG) and EcoRI (GAATTC) sites of *Escherichia coli* expression vector pET 33b (Novagen) and the stop codon (TAG).

IPTG (1 mM) was added to a culture solution of *Escherichia coli* (BL21 (DE3) strain, OD 600=0.8) transformed by each expression construct followed by incubating at 25° C. for 1 hour. The whole lysate was developed by SDS-PAGE and then stained with CBB, whereupon confirmed the induction of an expected molecular weight of protein. (refer to FIG. 14).

INDUSTRIAL APPLICABILITY

The present invention has clarified that the cause for onset of dilated cardiomyopathy is a point mutation of desmin gene which is a polypeptide related to T-tubule of striated muscle forming the cardiac muscle. Cardiomyopathy caused thereby is slow in onset, but once onset occurs, it results in serious diseases due to degradation of desmin and polypeptides related thereto.

The present invention provides a method for detecting and identifying the gene causative of such a dilated cardiomyopathy and is useful for preventing and treating a hereditary cardiomyopathy. The present invention further provides an animal model for disease having such a gene, and is useful not only for the development of preventive or therapeutic method for hereditary cardiomyopathy but also useful for the clarification of causes for various diseases relating to abnormality of striated muscle and for the establishment of preventive or therapeutic method therefor.

The invention claimed is:

1. An isolated Desmin gene of a Syrian hamster having a point mutation at the 571-position of the base sequence in the desmin cDNA translated region of the Syrian hamster wherein the gene consists of SEQ ID NO:1.

2. The gene of claim 1 wherein the point mutation is a mutation from G to A.

3. A method for detecting and identifying a point mutation at the 571-position of the base sequence in the desmin cDNA translated region of Syrian hamster wherein the gene consists of SEQ ID NO:1 and wherein PCR is employed.

4. The method of claim 3 wherein a determination is made wherein the point mutation is causative of heredity cardiomyopathy.

5. The method of claim 3 wherein a PCR primer is employed that comprises a base of a point mutation.

6. The method of claim 3 wherein the primer comprises a forward primer comprising the sequence of SEQ ID NO: 9 in combination with any of a reverse primer comprising the sequence of SEQ ID NO: 10, a reverse primer having a sequence of SEQ ID NO: 11, or a reverse primer having a sequence of SEQ ID NO: 12 .

* * * * *

SEQUENCE LISTING

```
<160> NUMBER OF SEQ ID NOS: 20

<210> SEQ ID NO 1
<211> LENGTH: 1627
<212> TYPE: DNA
<213> ORGANISM: Mesocricetus auratus
<220> FEATURE:
<221> NAME/KEY: CDS
<222> LOCATION: (82)..(1488)

<400> SEQUENCE: 1
cctcttcgta tccactctcc agccggctgc ctgcccgctg cctcctctgt gcgtctgccc      60
agcctcgtcc acgccgccac c atg agt cag gcc tac tct tcc agc cag cgg     111
                        Met Ser Gln Ala Tyr Ser Ser Ser Gln Arg
                         1               5                  10 gtg tcc tcc tac cgc cgc acc ttc ggt ggt gcc ccg agc ttc tcg ctg     159
Val Ser Ser Tyr Arg Arg Thr Phe Gly Gly Ala Pro Ser Phe Ser Leu
             15                  20                  25 ggc tct ccg ttg agc tct ccc gtg ttt cct cga gca ggc ttc ggc acc     207
Gly Ser Pro Leu Ser Ser Pro Val Phe Pro Arg Ala Gly Phe Gly Thr
         30                  35                  40 aag ggc tcc tcg agc tca gtg aca tcc cgc gtg tac cag gtg tcg cgc     255
Lys Gly Ser Ser Ser Ser Val Thr Ser Arg Val Tyr Gln Val Ser Arg
     45                  50                  55 acg tcg ggc ggg gcc ggg ggt ctg ggg tcg ctg cgg gcc agc cgg ctg     303
Thr Ser Gly Gly Ala Gly Gly Leu Gly Ser Leu Arg Ala Ser Arg Leu
 60                  65                  70 ggg agc acc cgc gcg cca tcc tat ggc gcg ggc gag ctt ctg gac ttc     351
Gly Ser Thr Arg Ala Pro Ser Tyr Gly Ala Gly Glu Leu Leu Asp Phe
 75                  80                  85                  90 tcg ctg gcc gac gcg gtg aac cag gag ttc ctg gcc acg cgc acc aac     399
Ser Leu Ala Asp Ala Val Asn Gln Glu Phe Leu Ala Thr Arg Thr Asn
                 95                 100                 105 gag aag gtg gag ctg caa gag ctc aat gac cgc ttc gcc aac tac atc     447
Glu Lys Val Glu Leu Gln Glu Leu Asn Asp Arg Phe Ala Asn Tyr Ile
            110                 115                 120 gag aaa gtg cgc ttc ttg gag cag cag aac gcc gcg ctc gcc gct gag     495
Glu Lys Val Arg Phe Leu Glu Gln Gln Asn Ala Ala Leu Ala Ala Glu
        125                 130                 135 gtc aac cgg ctc aag ggc cgc gag ccg acc cgg gtc gcc gag ctc tat     543
Val Asn Arg Leu Lys Gly Arg Glu Pro Thr Arg Val Ala Glu Leu Tyr
    140                 145                 150 gag gag gag atg cgc gag ctg cgg cgc cag gtg gag gtg ctc acc aac     591
Glu Glu Glu Met Arg Glu Leu Arg Arg Gln Val Glu Val Leu Thr Asn
155                 160                 165                 170 cag cgt gcc cgt gtc gac gtg gag cgc gac aac ttg atc gac gac ctc     639
Gln Arg Ala Arg Val Asp Val Glu Arg Asp Asn Leu Ile Asp Asp Leu
                175                 180                 185 cag agg ctc aag acc aag cta cag gag gaa atc caa ctg aga gaa gaa     687
Gln Arg Leu Lys Thr Lys Leu Gln Glu Glu Ile Gln Leu Arg Glu Glu
            190                 195                 200 gca gag aac aac ctg gct gcc ttc cga gcg gac gta gat gca gcc act     735
Ala Glu Asn Asn Leu Ala Ala Phe Arg Ala Asp Val Asp Ala Ala Thr
        205                 210                 215 ctg gct cgc atc gac cta gag cgc aga atc gaa tcg ctc aac gag gaa     783
Leu Ala Arg Ile Asp Leu Glu Arg Arg Ile Glu Ser Leu Asn Glu Glu
    220                 225                 230 atc gca ttc ctg aag aaa gtg cac gaa gag gag atc cgt gag ctt cag     831
Ile Ala Phe Leu Lys Lys Val His Glu Glu Glu Ile Arg Glu Leu Gln
```

```
                235                 240                 245                 250
gct cag ctt cag gaa cag cag gtc cag gtg gag atg gac atg tcc aag         879
Ala Gln Leu Gln Glu Gln Gln Val Gln Val Glu Met Asp Met Ser Lys
                    255                 260                 265 cca gac ctc aca gcg gcc ctc agg gac atc cgg gct cag tac gag acc         927
Pro Asp Leu Thr Ala Ala Leu Arg Asp Ile Arg Ala Gln Tyr Glu Thr
        270                 275                 280 att gcg gct aag aac atc tct gaa gct gag gag tgg tac aag tcc aag         975
Ile Ala Ala Lys Asn Ile Ser Glu Ala Glu Glu Trp Tyr Lys Ser Lys
                285                 290                 295 gtt tca gac ttg acc cag gca gcc aat aag aac aat gat gcc ctg cgc        1023
Val Ser Asp Leu Thr Gln Ala Ala Asn Lys Asn Asn Asp Ala Leu Arg
    300                 305                 310 cag gcc aag cag gag atg atg gag tac cga cac cag atc cag tcc tac        1071
Gln Ala Lys Gln Glu Met Met Glu Tyr Arg His Gln Ile Gln Ser Tyr
315                 320                 325                 330 acc tgc gag att gat gcc ctc aag ggc acc aat gac tcc ctg atg agg        1119
Thr Cys Glu Ile Asp Ala Leu Lys Gly Thr Asn Asp Ser Leu Met Arg
                335                 340                 345 cag atg aga gag ctg gag gat cgc ttt gcc agc gag gcc agt ggc tat        1167
Gln Met Arg Glu Leu Glu Asp Arg Phe Ala Ser Glu Ala Ser Gly Tyr
            350                 355                 360 cag gat aac att gca cgc ctg gag gag gag atc cgg cac ctg aag gat        1215
Gln Asp Asn Ile Ala Arg Leu Glu Glu Glu Ile Arg His Leu Lys Asp
        365                 370                 375 gag atg gcc cgc cac ctg cgg gag tac caa gac ctg ctc aat gtg aag        1263
Glu Met Ala Arg His Leu Arg Glu Tyr Gln Asp Leu Leu Asn Val Lys
    380                 385                 390 atg gcc ttg gat gtg gag att gcc acc tac cgc aag ctg ctg gag ggc        1311
Met Ala Leu Asp Val Glu Ile Ala Thr Tyr Arg Lys Leu Leu Glu Gly
395                 400                 405                 410 gag gag agc cgg atc aac ctt ccc atc cag acc ttc tct gct ctc aac        1359
Glu Glu Ser Arg Ile Asn Leu Pro Ile Gln Thr Phe Ser Ala Leu Asn
                415                 420                 425 ttc cga gaa acc agc cct gaa caa agg ggt tct gaa gtc cac acc aaa        1407
Phe Arg Glu Thr Ser Pro Glu Gln Arg Gly Ser Glu Val His Thr Lys
            430                 435                 440 aag acg gtg atg atc aag acc atc gag acc cgg gat gga gag gtc gtc        1455
Lys Thr Val Met Ile Lys Thr Ile Glu Thr Arg Asp Gly Glu Val Val
        445                 450                 455 agc gag gcc aca cag caa caa cac gag gtg ctc taagccagac actgtcctgg     1508
Ser Glu Ala Thr Gln Gln Gln His Glu Val Leu
    460                 465 tccccgtggt cactgcctcc tgaagccagc ctcttccact ctcggatgtc acacccagcc     1568
actttccttc actcacagaa tctgacccct cctcaccgat cacccctttg tggtcttca       1627

<210> SEQ ID NO 2
<211> LENGTH: 469
<212> TYPE: PRT
<213> ORGANISM: Mesocricetus auratus

<400> SEQUENCE: 2

Met Ser Gln Ala Tyr Ser Ser Gln Arg Val Ser Ser Tyr Arg Arg
 1               5                  10                  15

Thr Phe Gly Gly Ala Pro Ser Phe Ser Leu Gly Ser Pro Leu Ser Ser
                20                  25                  30

Pro Val Phe Pro Arg Ala Gly Phe Gly Thr Lys Gly Ser Ser Ser Ser
            35                  40                  45
```

```
Val Thr Ser Arg Val Tyr Gln Val Ser Arg Thr Ser Gly Gly Ala Gly
    50                  55                  60

Gly Leu Gly Ser Leu Arg Ala Ser Arg Leu Gly Ser Thr Arg Ala Pro
65              70                  75                  80

Ser Tyr Gly Ala Gly Glu Leu Leu Asp Phe Ser Leu Ala Asp Ala Val
                85                  90                  95

Asn Gln Glu Phe Leu Ala Thr Arg Thr Asn Glu Lys Val Glu Leu Gln
            100                 105                 110

Glu Leu Asn Asp Arg Phe Ala Asn Tyr Ile Glu Lys Val Arg Phe Leu
        115                 120                 125

Glu Gln Gln Asn Ala Ala Leu Ala Ala Glu Val Asn Arg Leu Lys Gly
    130                 135                 140

Arg Glu Pro Thr Arg Val Ala Glu Leu Tyr Glu Glu Met Arg Glu
145                 150                 155                 160

Leu Arg Arg Gln Val Glu Val Leu Thr Asn Gln Arg Ala Arg Val Asp
                165                 170                 175

Val Glu Arg Asp Asn Leu Ile Asp Asp Leu Gln Arg Leu Lys Thr Lys
            180                 185                 190

Leu Gln Glu Glu Ile Gln Leu Arg Glu Glu Ala Glu Asn Asn Leu Ala
        195                 200                 205

Ala Phe Arg Ala Asp Val Asp Ala Ala Thr Leu Ala Arg Ile Asp Leu
    210                 215                 220

Glu Arg Arg Ile Glu Ser Leu Asn Glu Glu Ile Ala Phe Leu Lys Lys
225                 230                 235                 240

Val His Glu Glu Glu Ile Arg Glu Leu Gln Ala Gln Leu Gln Glu Gln
            245                 250                 255

Gln Val Gln Val Glu Met Asp Met Ser Lys Pro Asp Leu Thr Ala Ala
        260                 265                 270

Leu Arg Asp Ile Arg Ala Gln Tyr Glu Thr Ile Ala Ala Lys Asn Ile
    275                 280                 285

Ser Glu Ala Glu Glu Trp Tyr Lys Ser Lys Val Ser Asp Leu Thr Gln
290                 295                 300

Ala Ala Asn Lys Asn Asn Asp Ala Leu Arg Gln Ala Lys Gln Glu Met
305                 310                 315                 320

Met Glu Tyr Arg His Gln Ile Gln Ser Tyr Thr Cys Glu Ile Asp Ala
            325                 330                 335

Leu Lys Gly Thr Asn Asp Ser Leu Met Arg Gln Met Arg Glu Leu Glu
        340                 345                 350

Asp Arg Phe Ala Ser Glu Ala Ser Gly Tyr Gln Asp Asn Ile Ala Arg
    355                 360                 365

Leu Glu Glu Glu Ile Arg His Leu Lys Asp Glu Met Ala Arg His Leu
    370                 375                 380

Arg Glu Tyr Gln Asp Leu Leu Asn Val Lys Met Ala Leu Asp Val Glu
385                 390                 395                 400

Ile Ala Thr Tyr Arg Lys Leu Leu Glu Gly Glu Glu Ser Arg Ile Asn
                405                 410                 415

Leu Pro Ile Gln Thr Phe Ser Ala Leu Asn Phe Arg Glu Thr Ser Pro
            420                 425                 430

Glu Gln Arg Gly Ser Glu Val His Thr Lys Lys Thr Val Met Ile Lys
        435                 440                 445

Thr Ile Glu Thr Arg Asp Gly Glu Val Val Ser Glu Ala Thr Gln Gln
    450                 455                 460

Gln His Glu Val Leu
```

<210> SEQ ID NO 3
<211> LENGTH: 240
<212> TYPE: DNA
<213> ORGANISM: Mesocricetus auratus

<400> SEQUENCE: 3
tacatcgaga aagtgcgctt cttggagcag cagaacgccg cgctcgccgc tgaggtcaac        60
cggctcaagg gccgcgagcc gacccgggtc gccgagctct atgaggagga gatgcgcgag       120
ctgcggcgcc aggtggaggt gctcaccaac cagcgtgccc gtgtcgacgt ggagcgcgac       180
aacttgatcg acgacctcca gaggctcaag gccaagtgag ggcacggcgc ctcctagatc       240

<210> SEQ ID NO 4
<211> LENGTH: 240
<212> TYPE: DNA
<213> ORGANISM: Mesocricetus auratus

<400> SEQUENCE: 4
tacatcgaga aagtgcgctt cttggagcag cagaacgccg cgctcgccgc tgaggtcaac        60
cggctcaagg gccgcgagcc gacccgggtc gccgagctct atgaggagga gatgcgcgag       120
ctgcggcgcc aggtggaggt gctcaccaac cagcgtgccc gtgtcgacgt ggagcgcgac       180
aacttgatcg acgacctcca gaggctcaag accaagtgag ggcacggcgc ctcctagatc       240

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Des5F,
      forward primer

<400> SEQUENCE: 5
tgcctcctct gtgcgtctgc                                                    20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Des5R,
      reverse primer

<400> SEQUENCE: 6
cgatcaagtt gtcgcgctcc                                                    20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Des3F,
      forward primer

<400> SEQUENCE: 7
ccagcgtgcc cgtgtcgacg                                                    20

<210> SEQ ID NO 8
<211> LENGTH: 20
<212> TYPE: DNA
<213> ORGANISM: Artificial Sequence
<220> FEATURE:

```
<223> OTHER INFORMATION: Description of Artificial Sequence: Des3R,
      reverse primer

<400> SEQUENCE: 8
ggtgtgacat ccgagagtgg                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: DesF,
      forward primer

<400> SEQUENCE: 9
gaaagtgcgc ttcttggagc                                              20

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: DesGR,
      reverse primer

<400> SEQUENCE: 10
gtgccctcac ttggc                                                   15

<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: DesTR,
      reverse primer

<400> SEQUENCE: 11
gtgccctcac ttggt                                                   15

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: DesTR,
      reverse primer

<400> SEQUENCE: 12
ccgtgccctc acttggt                                                 17

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Head,
      HD-F:forward primer

<400> SEQUENCE: 13
ggcatatgag tcaggcctac tc                                           22

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Head,
```

```
            HD-R:reverse primer

<400> SEQUENCE: 14
ccgaattcta gaactcctgg ttcaccg                                      27

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Coil-1,
      CL1-F:forward primer

<400> SEQUENCE: 15
ggcatatgct ggccacgcgc accaac                                       26

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Coil-1,
      CL1-R:reverse primer

<400> SEQUENCE: 16
ccgaattcta gtccatctcc acctggac                                     28

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Coil-2,
      CL2-F:forward primer

<400> SEQUENCE: 17
ggcatatgtc caagccagac ctc                                          23

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: Coil-2,
      CL2-R:reverse primer

<400> SEQUENCE: 18
ccgaattcta ctccacatcc aaggccatc                                    29

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Tail,
      TL-F:forward primer

<400> SEQUENCE: 19
ggcatatgat tgccacctac cgcaag                                       26

<210> SEQ ID NO 20
<211> LENGTH: 25
<212> TYPE: DNA
<213> ORGANISM: Artificial Sequence
```

```
-continued

<220> FEATURE:
<223> OTHER INFORMATION: Description of Artificial Sequence: Tail,
      TL-R:reverse primer

<400> SEQUENCE: 20
ccgaattcta gagcacctcg tgttg                                            25
```